(12) United States Patent
Schlicke et al.

(10) Patent No.: US 11,293,900 B2
(45) Date of Patent: Apr. 5, 2022

(54) METHOD FOR DETECTING AN ANALYTE BASED ON THE DETECTION OF A CHANGE OF THE MECHANICAL PROPERTIES OF A FREESTANDING NANOPARTICLE COMPOSITE MATERIAL

(71) Applicant: Fraunhofer-Gesellschaft zur Foerderung der angewandten Forschung e.V., Munich (DE)

(72) Inventors: Hendrik Schlicke, Hamburg (DE); Tobias Vossmeyer, Hamburg (DE); Malte Behrens, Hamburg (DE); Sophia Caroline Bittinger, Hamburg (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 109 days.

(21) Appl. No.: 16/496,994

(22) PCT Filed: Mar. 22, 2018

(86) PCT No.: PCT/EP2018/057280
§ 371 (c)(1),
(2) Date: Sep. 24, 2019

(87) PCT Pub. No.: WO2018/172450
PCT Pub. Date: Sep. 27, 2018

(65) Prior Publication Data
US 2021/0102919 A1    Apr. 8, 2021

(30) Foreign Application Priority Data
Mar. 24, 2017 (GB) .................................. 1704749.9

(51) Int. Cl.
*G01N 29/02* (2006.01)
*G01N 29/036* (2006.01)
(Continued)

(52) U.S. Cl.
CPC ......... *G01N 29/022* (2013.01); *G01N 29/036* (2013.01); *G01N 29/4436* (2013.01);
(Continued)

(58) Field of Classification Search
CPC ............. G01N 29/022; G01N 29/4436; G01N 29/036; G01N 33/0032; G01N 2291/106;
(Continued)

(56) References Cited

U.S. PATENT DOCUMENTS 6,458,327 B1   10/2002   Vossmeyer
2004/0211251 A1   10/2004   Lee et al.
(Continued)

FOREIGN PATENT DOCUMENTS

EP    1215485 A1   6/2002
EP    2589958 A1   5/2013
WO   WO2005100965 A1   10/2005

OTHER PUBLICATIONS

International Search Report and Written Opinion of the International Searching Authority, dated Jun. 22, 2018, with respect to International Application No. PCT/EP2018/057280.
(Continued)

*Primary Examiner* — Tarun Sinha
(74) *Attorney, Agent, or Firm* — Scott R. Cox

(57) ABSTRACT

The present invention relates to a method for detecting an analyte, which is based on the detection of a signal caused by a change of the mechanical properties of a permeable freestanding nanoparticle composite. The present invention
(Continued)

Figure 1:
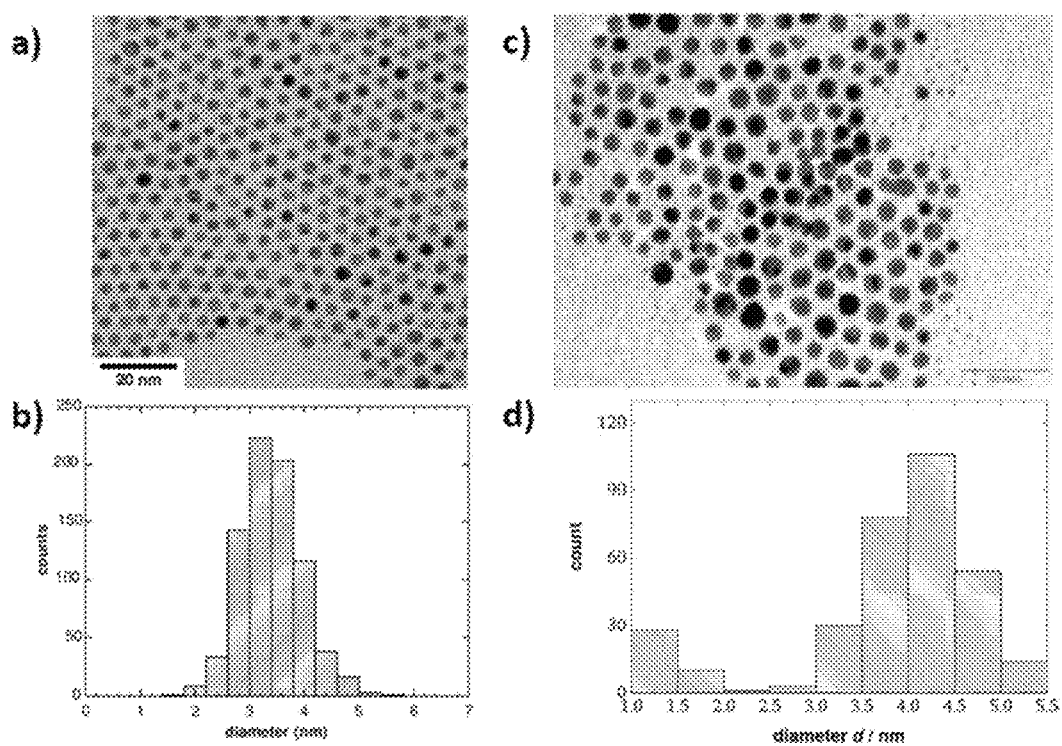

also relates to a method for determining the concentration of and/or recognizing an analyte.

16 Claims, 8 Drawing Sheets

(51) Int. Cl.
*G01N 29/44* (2006.01)
*G01N 33/00* (2006.01)

(52) U.S. Cl.
CPC ... *G01N 33/0032* (2013.01); *G01N 2291/014* (2013.01); *G01N 2291/0256* (2013.01); *G01N 2291/02827* (2013.01); *G01N 2291/106* (2013.01)

(58) Field of Classification Search
CPC ... G01N 2291/02827; G01N 2291/014; G01N 2291/0256
See application file for complete search history.

(56) References Cited

U.S. PATENT DOCUMENTS

| | | | | |
|---|---|---|---|---|
| 2005/0262943 | A1* | 12/2005 | Claydon | G01N 29/022 73/579 |
| 2006/0251543 | A1* | 11/2006 | Koratkar | B82Y 15/00 422/98 |
| 2010/0181871 | A1* | 7/2010 | Daniel | G01L 1/16 310/338 |
| 2010/0317124 | A1 | 12/2010 | Kim et al. | |
| 2011/0031566 | A1 | 2/2011 | Kim et al. | |
| 2012/0007099 | A1* | 1/2012 | Liu | G01N 27/125 257/76 |
| 2013/0041235 | A1* | 2/2013 | Rogers | A61B 5/1107 600/306 |
| 2013/0320467 | A1* | 12/2013 | Buchanan | G06F 3/045 257/419 |
| 2016/0123930 | A1* | 5/2016 | Noyce | G01N 29/022 436/501 |

OTHER PUBLICATIONS

Hendrik Schlicke et al., "Freestanding films of crosslinked gold nanoparticles prepared via layer-by-layer spin-coating", Nanotechnology, UK, (Jun. 27, 2011), vol. 22, No. 30.

Hendrik Schlicke et al., "Electrostatically driven drumhead resonators based on freestanding membranes of cross-linked gold nanoparticles", Nanoscale, UK, (Sep. 21, 2016), vol. 8, No. 35.

United Kingdom Search Report, dated Jul. 24, 2017, with respect to Priority application No. GB1704749.9.

International Preliminary Report on Patentability of the International Searching Authority, dated Sep. 24, 2019, with respect to International Application No. PCT/EP2018/057280.

Gor Gennady Y et al: "Adsorption-induced deformation of nanoporous materials—A review", Applied Physics Reviews, vol. 4, No. 1, Feb. 24, 2017.

European Search Report dated Feb. 1, 2021 with respect to corresponding European patent application No. 18712611.5 (international application No. PCT/EP2018/057280).

* cited by examiner

METHOD FOR DETECTING AN ANALYTE BASED ON THE DETECTION OF A CHANGE OF THE MECHANICAL PROPERTIES OF A FREESTANDING NANOPARTICLE COMPOSITE MATERIAL

The present invention relates to a method for detecting an analyte, which is based on the detection of a sensor signal that is caused by a change of the mechanical properties of a permeable freestanding nanoparticle composite material. The present invention also relates to a method for quantifying and/or recognizing an analyte.

BACKGROUND OF THE INVENTION

The detection of analytes, in particular analytes in the gas phase, with high sensitivity and selectivity plays a crucial role in various fields of activities. For instance, the detection of analytes with high sensitivity and selectivity is essential in environmental analysis, e.g. for the detection of pollutants or toxic species in case of unwanted spills and leakages. Furthermore, the detection of analytes is also essential in the fields of security/public safety, e.g. to detect harmful substances or explosives, in healthcare or medicine, e.g. for breath analysis and other diagnostic purposes, and in quality management, e.g. for monitoring the quality of goods such as comestible or medicinal goods. Small sensors (also called "sensing devices") based on various signal transduction mechanisms such as optical, electrical, or electromechanical mechanisms have therefore been developed.

"Chemiresistors" (also called "chemiresistive sensors") can detect an analyte, e.g. an analyte in the gas phase, by measuring a change in the electrical resistance, e.g. of a conductive thin film. Chemiresistors using thin films of metal oxides or, more recently, conductive nanomaterials such as ligand-capped or molecularly cross-linked metal nanoparticles have attracted significant interest due to their sensitivity and tunable chemical selectivity (cf. Ibañez F J et al. Chemiresistive Sensing with Chemically Modified Metal and Alloy Nanoparticles *Small* 2012, vol. 8(2), pages 174-202).

Furthermore, electromechanical chemical sensors, which can detect analytes based on a change of the capacitance of a conductive thin film arranged with a counter electrode, have also gained attention in the field of microelectromechanical systems (MEMS).

EP 1 215 485 B1 discloses a sensor comprising a substrate and a nanoparticle film formed thereon, the nanoparticle film comprising a network of nanoparticles interlinked with each other. The sensor can be used in a method for detecting an analyte by measuring e.g. a change of the electrical resistance of the nanoparticle film.

US 2004/0211251 A1 discloses a thin membrane transducer, e.g. a sensor, comprising a thin membrane of elastomeric material, which is coated on its outer surface with a specific reaction agent offering binding sites for an analyte. The membrane can be deflected as a result of surface stress induced by the interaction of an analyte with the reaction agent on the surface of the membrane. In turn, the deflection of the membrane leads to a change of capacitance, which can be measured by a detection means.

US 2010/0317124 A1 discloses a sensor comprising a substrate having at least one opening (aperture), a thin metal-containing membrane associated with the opening(s), and at least one electrode. The surface of the membrane is configured to interact with and to detect an analyte. Specifically, the interaction of an analyte with the surface of the membrane, e.g. adsorption, causes the membrane to deflect, resulting in a change of the distance between the membrane and the electrode. The change of the distance between the membrane and the electrode, in turn, leads to a change of capacitance thus allowing the detection of the analyte. A sensor based on a similar mechanism is also described in US 2011/0031566 A1.

Other types of electromechanical chemical sensors have also been developed. One prominent example of such sensor is the well-known and commonly used "quartz crystal microbalance" (QCM), which has evolved to a standard tool for the detection of analytes, e.g. analytes in the gas phase. QCM sensors measure a mass variation per unit area by measuring a change in resonance frequency of a quartz crystal resonator. Moreover, electromechanical sensors comprising microcantilevers or beams, coated with specific materials capable of selectively absorbing an analyte have also been described. Microcantilever-based sensors can detect an analyte based on the static deflection of a cantilever associated with a volume change (swelling or contraction) of a coating material due to analyte sorption. Also, a vibrating cantilever can be used as a gravimetric sensor by detecting a change in its resonance frequency upon sorption of the analyte.

However, the sensors and sensor arrays described in the prior art (i.e. chemical sensors, including chemiresistors, electromechanical sensors and arrays thereof) often have limited sensitivity, thus rendering difficult the detection of analytes, e.g. analytes in the gas phase, in very low concentrations. Furthermore, the sensors described in the prior art often lack chemical selectivity and are hardly tunable when it comes to detecting and/or recognizing a specific analyte.

In addition to the individual sensor types hereinbefore discussed, the combination of sensors (chemical sensors, including chemiresistive or electromechanical sensors) with different chemical selectivities in "sensor arrays" is also of great interest. For instance, sensors having different selectivities have been combined in arrays so as to form "electronic noses", which produce a characteristic signal pattern that can be used to identify a specific (target) analyte.

In principle, the sensitivity and chemical selectivity of a sensor depends on its sensing mechanism, the method used for signal transduction, and the chemical nature of the material(s) used to interact with the analyte. It is furthermore advantageous to combine individual sensors having different sensing mechanisms and selectivities for the purpose of recognizing a specific analyte or a specific mixture of analytes, e.g. a gas mixture.

There is hence a need for novel sensing mechanisms and transduction principles, which can be used to achieve sensors and sensor arrays having high sensitivity and/or tunable chemical selectivity for different analytes. Moreover, there is also a need for novel methods using these novel sensing mechanisms and transduction principles for detecting, quantifying and/or recognizing analytes, in particular analytes in the gas phase.

It is thus an object of the present invention to provide a method which allows the detection of an analyte or a group of analytes, e.g. an analyte in the gas phase, with high sensitivity and/or chemical selectivity (for the individual analyte or a specific mixture of analytes).

It is a further object of the present invention to provide a method which allows the quantification of an analyte or a group of analytes with sufficient preciseness and/or chemical selectivity.

According to one further preferred aspect of the present invention, the method uses an array of individual sensors to produce a signal pattern allowing the identification and optionally the quantification of an unknown analyte or a group of analytes. The array may also comprise sensors acquiring environmental data such as humidity, pressure and temperature. The humidity, pressure and temperature data may for instance be used to increase the preciseness of the identification and optionally the quantification of an unknown analyte or a group of analytes.

SUMMARY OF THE PRESENT INVENTION

The present invention relates to a method for detecting an analyte with a chemical sensor comprising the steps of:
(i) exposing a chemical sensor comprising a permeable freestanding nanoparticle composite material to an analyte, e.g. an analyte in the gas phase; and
(ii) measuring a sensor signal that is caused by a change of the elastic modulus and/or pre-stress of the freestanding nanoparticle composite material by a detection means.

The present invention also relates to the use of the method hereinbefore mentioned for determining the concentration of an analyte, the method further comprising the steps of:
(iii) calibrating a chemical sensor comprising a permeable freestanding nanoparticle composite material by measuring the sensor signal when exposing the chemical sensor to a reference sample of an analyte at various known concentrations; and
(iv) comparing the sensor signal measured by exposing the chemical sensor to a test sample of the analyte to the calibration data measured in step (iii) in order to determine the concentration of analyte in the test sample.

The present invention also relates to the use of the method hereinbefore mentioned for recognizing an analyte, the method further comprising the steps of:
(v) optionally adjusting the chemical selectivity of the freestanding nanoparticle composite material to an analyte to be recognized before (i) exposing the chemical sensor to the analyte;
(vi) calibrating the chemical sensor by measuring the sensor signal when exposing the chemical sensor to a reference sample of a known analyte; and
(vii) comparing the sensor signal, such as the signal shape (response kinetic), measured by exposing the chemical sensor to a test sample of an analyte to the calibration data measured in step (vi) in order to recognize the analyte in the test sample.

The present invention also relates to a method for recognizing an analyte, which comprises exposing an array of chemical sensors comprising a freestanding nanoparticle composite material and/or such sensors combined with chemical or physical sensors having a different signal transduction mechanism.

The present invention includes the following embodiments ("Items"):
1. Method for detecting an analyte with a chemical sensor, comprising the steps of:
   (i) exposing a chemical sensor comprising a permeable freestanding nanoparticle composite material to an analyte; and
   (ii) measuring a sensor signal that is caused by a change of the elastic modulus and/or pre-stress of the freestanding nanoparticle composite material by a detection means.
2. The method of item 1, wherein the chemical sensor comprises:
   a substrate;
   optionally one or more insulating layers on at least one side of said substrate; and
   optionally two or more electrodes;
   wherein the substrate and/or insulating layers preferably comprises one or more microcavities, onto which the freestanding nanoparticle composite material is suspended.
3. The method of item 1 or 2, wherein the freestanding nanoparticle composite material is suspended as a cantilever, a single- or multiple-clamped beam, a string, a plate, or a membrane, preferably as a membrane;
   wherein the membrane preferably has a thickness lower than 1000 nm, more preferably lower than 500 nm, more preferably lower than 200 nm.
4. The method of any of items 1, 2 and 3, wherein the freestanding nanoparticle composite material comprises nanoparticles formed from:
   (a) a metal, preferably a noble metal such as Au, Pt, Ag, Pd, a coinage metal such as Cu, Ni, Co, Mn, Fe, and alloys thereof;
   (b) a metal oxide such as iron oxides, (including $Fe_3O_4$ and $Fe_2O_3$), $SnO_2$, $TiO_2$, and indium tin oxides;
   (c) a semiconductor, preferably a II/VI semiconductor such as CdS, CdSe, CdTe, ZnS, ZnSe, ZnTe, HgS, HgSe, HgTe, and/or a III/V semiconductor such as GaAs, InP;
   (d) carbon such as carbon black, carbon nanotubes, graphite, a mono- or multilayered two-dimensional carbon material such as flakes of graphene, graphene oxide, or reduced graphene oxide;
   (e) a metal chalcogenide, in particular a transition metal chalcogenide such as $MoS_2$, a mono- or multilayered two-dimensional metal chalcogenide material such as flakes of a transition metal chalcogenide; or
   any combination thereof such as core-shell, core-shell-shell or Janus-type nanoparticles; and
   the freestanding nanoparticle composite material may contain a combination of such nanoparticles.
5. The method of item 4, wherein the nanoparticles are spherical, polyhedral, star-shaped or elongated e.g. rod-, tube- or fiber-shaped, plate or sheet-like and preferably have in at least one dimension a length lower than 100 nm, more preferably lower than 50 nm, more preferably lower than 30 nm; and
   wherein the nanoparticles preferably are essentially spherical or polyhedral particles having a respective average diameter or length in at least one dimension lower than 100 nm, preferably lower than 50 nm, more preferably lower than 30 nm.
6. The method of any of items 1, 2, 3, 4 and 5, wherein the freestanding nanoparticle composite material comprises a matrix in which the nanoparticles are dispersed and/or interconnected with each other;
   wherein the matrix comprises a material selected from the group consisting of:
   A) organic polymers;
   B) polysiloxanes;
   C) organic ligands, in particular mono-, bi- or polyfunctional organic ligands that are able to attach to the surface of the nanoparticles with at least one functional group, such functional group(s) preferably being selected from the groups comprising sulfur-containing functionality, or nitrogen-containing functionality, or phosphorus-containing functionality, or oxygen-containing functionality;
   D) organic cross-linkers, in particular bi- or polyfunctional organic cross-linkers that are able to attach to the surface of the nanoparticles with at least two functional groups, such functional groups preferably being selected from the groups comprising sulfur-containing functionality, or nitrogen-containing functionality, or phosphorus-containing functionality, or oxygen-containing functionality;
and combinations thereof.

7. The method of item 6, wherein the matrix is attached to the surface of the nanoparticles via covalent bonds, ionic bonds, coordinative covalent (dipolar) bonds and/or multiple dipolar interactions; and
wherein the matrix is preferably attached to the surface of the nanoparticles via carbon-to-nanoparticle bonds such as carbon-to-metal bonds or carbon-carbon bonds, or via one or more functional groups, such functional group(s) preferably being selected from thiol, disulfide, carbamate, thiocarbamate, dithiocarbamate, amino, carboxylic acid, hydroxyl, polyether, isocyanide, dihydroxyphenyl, phosphine, phosphine oxide, and phosphonic acid groups.

8. The method of items 6 or 7, wherein the nanoparticles are cross-linked with a bi- or polyfunctional organic cross-linker having functional groups that are able to attach to the surface of the nanoparticles such as thiol, disulfide, amino, carboxylic acid, thiocarbamate, dithiocarbamate, hydroxyl, isocyanide, dihydroxyphenyl, phosphine, phosphine oxide, and phosphonic acid groups.

9. The method of any of items 1, 2, 3, 4, 5, 6, 7 and 8, wherein the sensor signal that is caused by a change of elastic modulus and/or pre-stress of the freestanding nanoparticle composite material is detected by measuring a change in the structure and/or topography and/or shape and/or size of the composite material;
wherein the change in the structure and/or topography and/or shape and/or size of the composite material is preferably detected by detecting light reflected and/or emitted from and/or scattered by the composite material.

10. The method of any of items 1, 2, 3, 4, 5, 6, 7 and 8, wherein the sensor signal that is caused by a change of elastic modulus and/or pre-stress of the freestanding nanoparticle composite material is detected by:
applying a quasi-static actuating force on the composite material, such as an electrostatic force, a piezoelectric force, or a magnetic force; and by
measuring the response of the composite material to the actuating force.

11. The method of any of items 1, 2, 3, 4, 5, 6, 7 and 8, wherein the sensor signal that is caused by a change of elastic modulus and/or pre-stress of the freestanding nanoparticle composite material is detected by:
applying a dynamic actuating force e.g. an electrostatic force induced by an alternating (AC) electric field preferably having a frequency between 1 kHz to 10 GHz, such that the composite material oscillates at one of its resonance frequencies; and by
measuring a shift of the resonance frequency and/or any change in amplitude and/or phase at a given frequency.

12. The method of any of items 1, 2, 3, 4, 5, 6, 7, 8, 9, 10 and 11, wherein the sensor signal that is caused by a change of elastic modulus and/or pre-stress of the freestanding nanoparticle composite material is detected by:
measuring a change of a physical property which can be detected without applying an actuating force; and/or by measuring a change of the composite material's response to a quasi-static actuating force, and/or a dynamic actuating force.

13. The method of any of items 10, 11 and 12, wherein the response of the freestanding nanoparticle composite material to the actuating force applied thereon is measured by:
($\alpha$) detecting light reflected and/or emitted from and/or scattered by the composite material; and/or by
($\beta$) measuring a change of the electrical resistance/impedance of the composite material; and/or by
($\gamma$) measuring a change of the capacitance of the composite material arranged with one or more proximate electrodes; and/or by
($\delta$) measuring the magnetic field in proximity of the composite material.

14. The method of any of items 1, 2, 3, 4, 5, 6, 7, 8, 9, 10, 11, 12 and 13, which is used for determining the concentration of an analyte, wherein the method further comprises the steps of:
(iii) calibrating a chemical sensor comprising a permeable freestanding nanoparticle composite material by measuring the sensor signal when exposing the chemical sensor to a reference sample of an analyte at various known concentrations; and
(iv) comparing the sensor signal measured by exposing the chemical sensor to a test sample of the analyte to the calibration data measured in step (iii) in order to determine the concentration of analyte in the test sample.

15. The method of any of items 1, 2, 3, 4, 5, 6, 7, 8, 9, 10, 11, 12, 13 and 14, which is used for recognizing an analyte, wherein the method further comprises the steps of:
(v) optionally adjusting the chemical selectivity of the freestanding nanoparticle composite material to an analyte to be recognized before (i) exposing the chemical sensor to the analyte;
(vi) calibrating the chemical sensor comprising a permeable freestanding nanoparticle composite material by measuring the sensor signal when exposing the chemical sensor to a reference sample of a known analyte; and
(vii) comparing the sensor signal measured by exposing the chemical sensor to a test sample of an analyte to the calibration data measured in step (vi) in order to recognize the analyte in the test sample.

16. The method of any of items 1, 2, 3, 4, 5, 6, 7, 8, 9, 10, 11, 12, 13, 14 and 15, wherein the analyte is in the fluid phase, preferably in the gas phase.

17. The method of any of items 1, 2, 3, 4, 5, 6, 7, 8, 9, 10, 11, 12, 13, 14, 15 and 16, wherein the method comprises exposing an array of chemical sensors comprising at least two chemical sensors, preferably a plurality of chemical sensors, to an analyte thus affording a signal pattern that allows recognition of the analyte;
wherein the individual chemical sensors comprise a permeable freestanding nanoparticle composite material and differ from each other in the type of nanoparticles and/or the chemical composition of the matrix in their respective freestanding nanoparticle composite material, and/or the thickness, geometry, or geometric arrangement of their respective freestanding nanoparticle composite material, and/or differ from each other in their respective detection mode.

18. The method of any of items 1, 2, 3, 4, 5, 6, 7, 8, 9, 10, 11, 12, 13, 14, 15, 16 and 17, wherein the chemical sensor comprising a permeable freestanding nanoparticle composite material or an array of such chemical sensors is combined with at least one other chemical or physical sensor having a different signal transduction mechanism.

Where the present description refers to "preferred" embodiments/features, combinations of these "preferred" embodiments/features shall also be deemed as disclosed as long as this combination of "preferred" embodiments/features is technically meaningful.

Hereinafter, in the present description of the invention and the claims, the use of the term "comprising" should be understood as disclosing, as a more restricted embodiment, the term "consisting of" as well, as long as this is technically meaningful.

FIGURES

FIG. 1—(a) Transmission electron microscopy (TEM) image of the gold nanoparticles used to prepare the nanoparticle composite material, which was used for the fabrication of sensor CS1. (b) Size histogram of the nanoparticle sample shown in (a). (c) TEM image of the gold nanoparticles used to prepare the nanoparticle composite material, which was used for the fabrication of sensor CS2. (d) Size histogram of the nanoparticle sample shown in (c).

Figure 2:
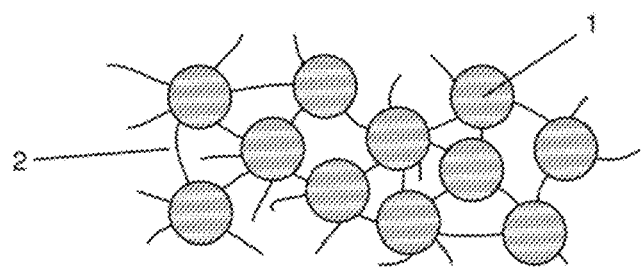

FIG. 2—Schematic drawing showing the structure of a cross-linked nanoparticle composite material according to one embodiment of the method of the present invention.

Figure 3:
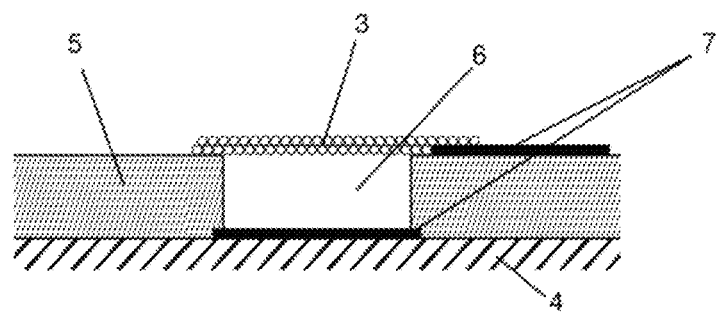

FIG. 3—Schematic drawing showing a chemical sensor comprising a freestanding nanoparticle composite material according to one embodiment of the method of the present invention.

FIGS. 2 and 3 give a survey on the terminology used with respect to the chemical sensor used in the method of the present invention. In FIGS. 2 and 3 the following reference numbers represent:
(1) Nanoparticles
(2) Cross-linkers
(3) Freestanding nanoparticle composite material
(4) Substrate
(5) Insulating layer
(6) Microcavity
(7) Electrodes FIG. 4—Examples of freestanding nanoparticle composite materials according to the present invention. (a) Nanoparticle composite material forming a freestanding cantilever. The nanoparticle composite material is contacted by electrode A and the cantilever is positioned in proximity (above) of electrode B. (b) Nanoparticle composite material forming a freestanding membrane covering only a part of a microcavity (bridge). The nanoparticle composite material is contacted by electrodes A and C, and the bridge is positioned in proximity (above) of electrode B. (c) Nanoparticle composite material forming a circular freestanding membrane completely covering a microcavity. The nanoparticle composite material is contacted by electrode A and positioned in proximity (above) of electrode B.

Figure 5:
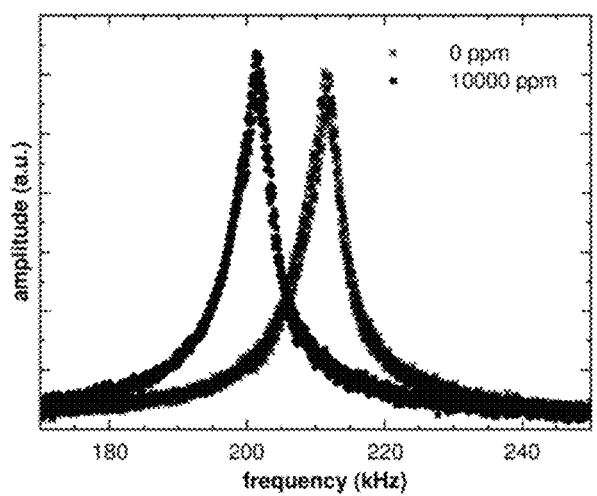

FIG. 5—Amplitude spectra showing the fundamental resonance frequencies of a freestanding gold nanoparticle composite material (membrane) under nitrogen gas (crosses) and nitrogen gas enriched with 10000 ppm (partial pressure: 20 Pa) of toluene (points) at a total pressure of 20 mbar.

Figure 6:
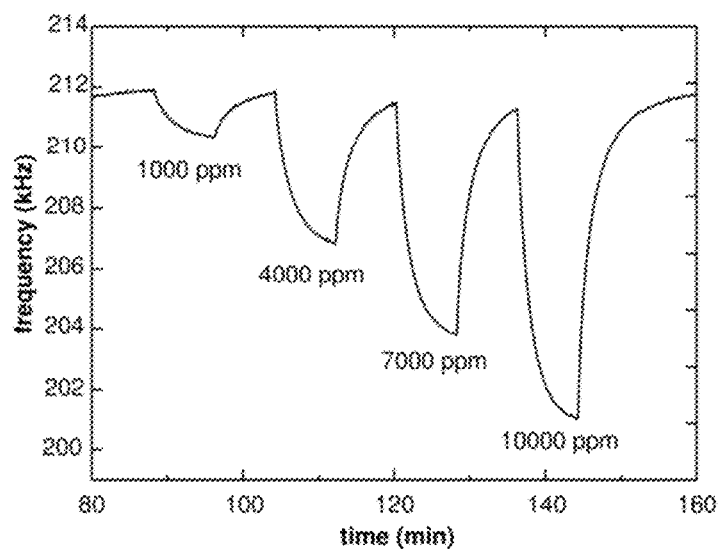

FIG. 6—Frequency-time trace showing the shift of the fundamental resonance frequency $\Delta_0(t)$ of a freestanding gold nanoparticle composite material (membrane) under a 20 mbar atmosphere of nitrogen gas. The observed transients are frequency shifts induced by dosing the membrane with 8 min pulses of nitrogen gas enriched with increasing concentrations (partial pressures) of toluene, i.e. 1000 ppm (2 Pa), 4000 ppm (8 Pa), 7000 ppm (14 Pa), and 10000 ppm (20 Pa). After each dose of analyte/nitrogen mixture the sensor cell was purged with pure nitrogen while maintaining the total pressure of 20 mbar.

Figure 7:
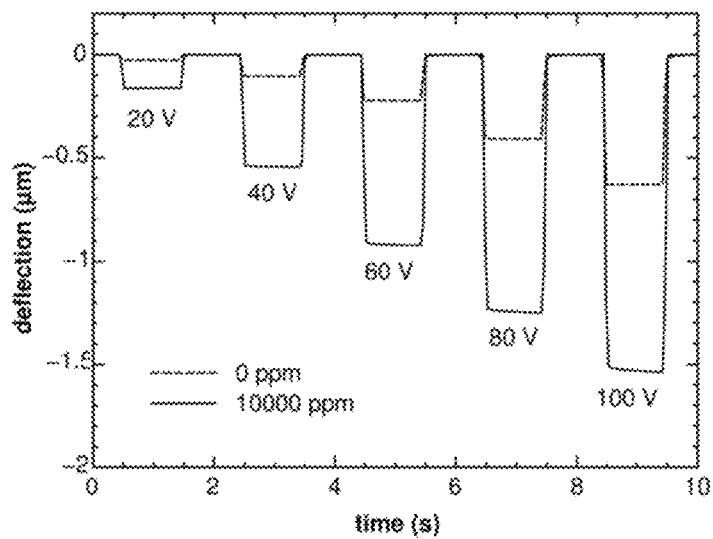

FIG. 7—Deflection-time trace showing the deflection of a freestanding gold-nanoparticle composite material (membrane) actuated using 1 second pulses of increasing direct (DC) voltages (i.e. 20 V, 40 V, 60 V, 80 V and 100 V) under nitrogen gas (dashed line) and nitrogen gas enriched with 10000 ppm of toluene (solid line). The total pressure in the cell was ~1 bar.

Figure 8:
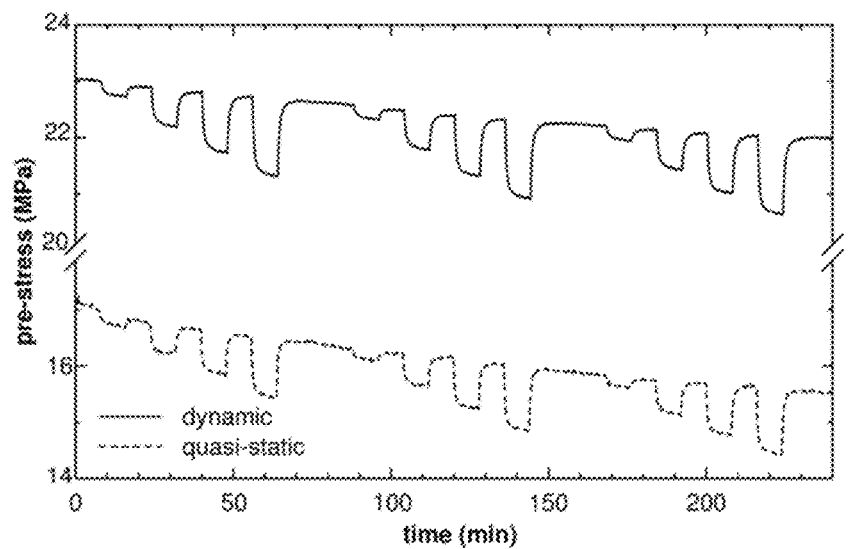

FIG. 8—Pre-stress-time trace showing the pre-stress of a freestanding gold-nanoparticle composite material (membrane) measured using a quasi-static actuating force (i.e. groups of 1 second pulses of increasing DC voltages: 20 V, 40 V, 60 V, 80 V and 100 V; dashed line) and a dynamic actuating force (i.e. a frequency $f_d$ swept sine drive signal; solid line) under nitrogen gas. The transients, revealing a reversible decrease in pre-stress, were observed when dosing the membrane with nitrogen enriched with increasing concentrations (partial pressures) of toluene, i.e. 1000 ppm (2 Pa), 4000 ppm (8 Pa), 7000 ppm (14 Pa), and 10000 ppm (20 Pa). The total pressure in the cell was 20 mbar and kept constant during the experiment.

Figure 9:
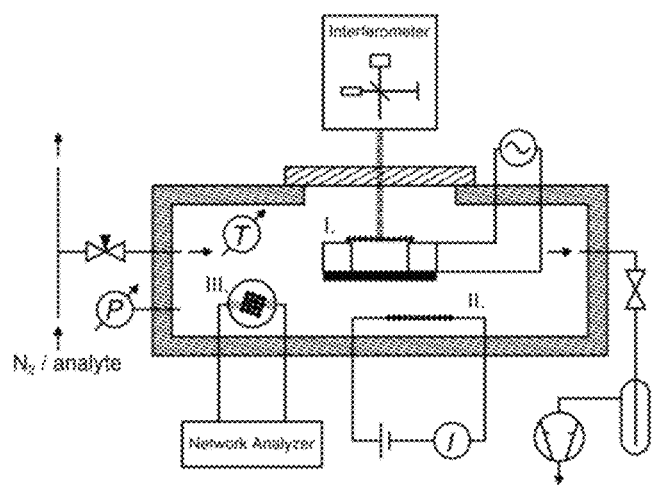

FIG. 9—Schematic of the experimental setup including a printed circuit board mounted with (I) a chemical sensor comprising a freestanding nanoparticle composite material (membrane) with interferometric deflection readout (according to the invention), (II) a chemiresistor comprising a nanoparticle composite material (prior art), and (III) a quartz crystal microbalance coated with a nanoparticle composite material (prior art), each connected to respective suitable readout electronics. The printed circuit board with the three chemical sensors was placed into a sensor test cell equipped with additional pressure and temperature sensors. The sensor test cell was connected to a vacuum pump and a peripheral gas calibration system enabling the introduction of nitrogen gas mixed with solvent vapors at defined concentrations.

Figure 10:
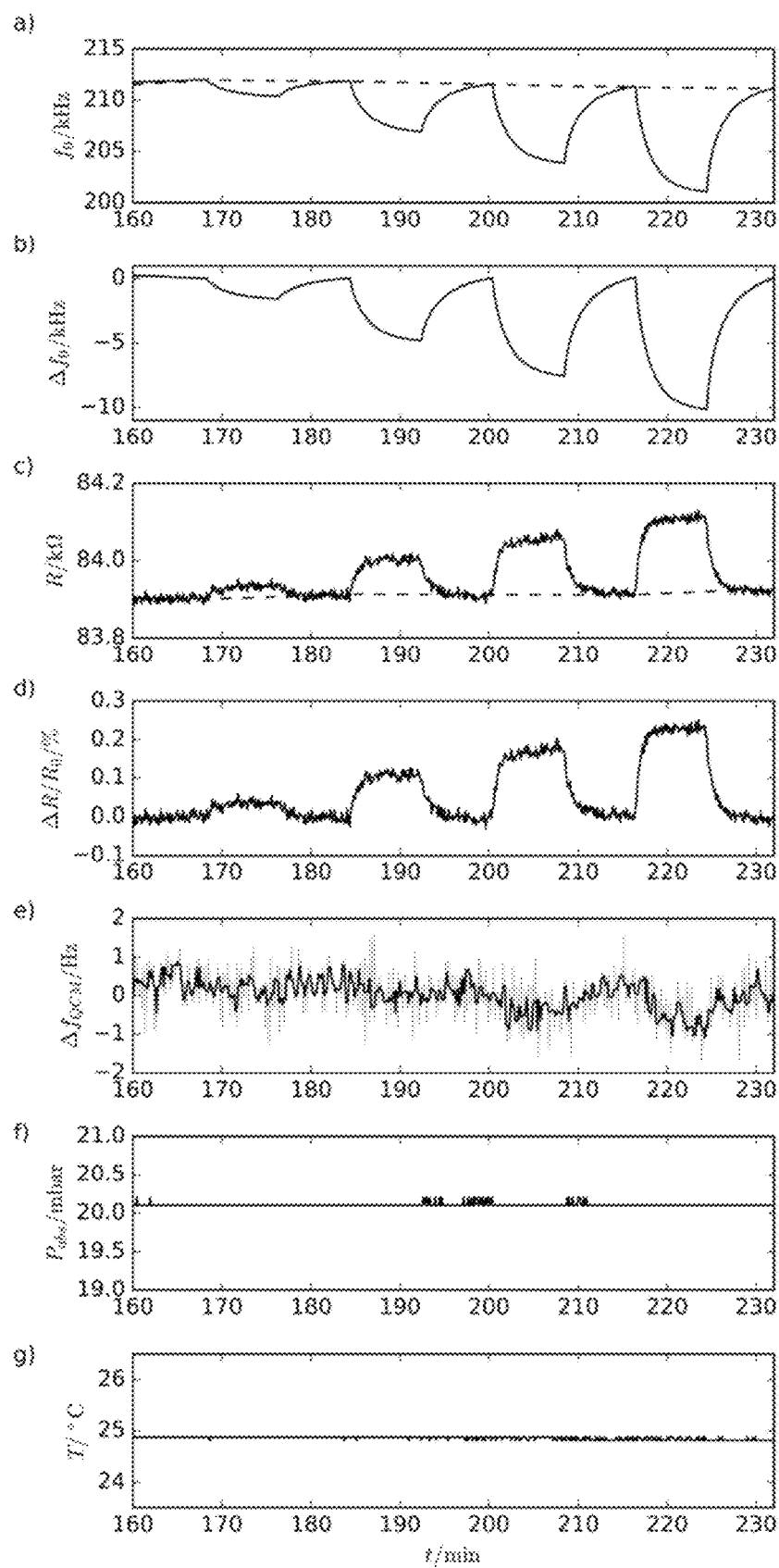

FIG. 10—Time traces showing the fundamental resonance frequency $f_0$ of a chemical sensor according to the invention comprising a freestanding nanoparticle composite material (membrane) under nitrogen gas dosed with 8 min pulses of nitrogen gas enriched with increasing concentrations (partial pressures) of toluene, i.e. 1000 ppm (2 Pa), 4000 ppm (8 Pa), 7000 ppm (14 Pa), and 10000 ppm (20 Pa) (trace (a)), the corresponding fundamental resonance frequency shift $\Delta f_0$ of the chemical sensor obtained by subtracting the baseline (dashed line in (a)) from $f_0$ (trace (b)), the electrical resistance R of a chemiresistor comprising a nanoparticle composite material (trace (c)—prior art), the corresponding relative electrical resistance change $\Delta R/R_0$ (with $\Delta R = R - R_0$ and $R_0$ being the baseline resistance represented by the dashed line in (c)) (trace (d)—prior art), and the fundamental resonance frequency shift $\Delta f_{QCM}$ of a quartz crystal microbalance coated with a nanoparticle composite material (trace (e)—prior art). Traces (f) and (g) display the total pressure $P_{abs}$ and the temperature T, respectively, measured within the sensor test cell.

Figure 11:
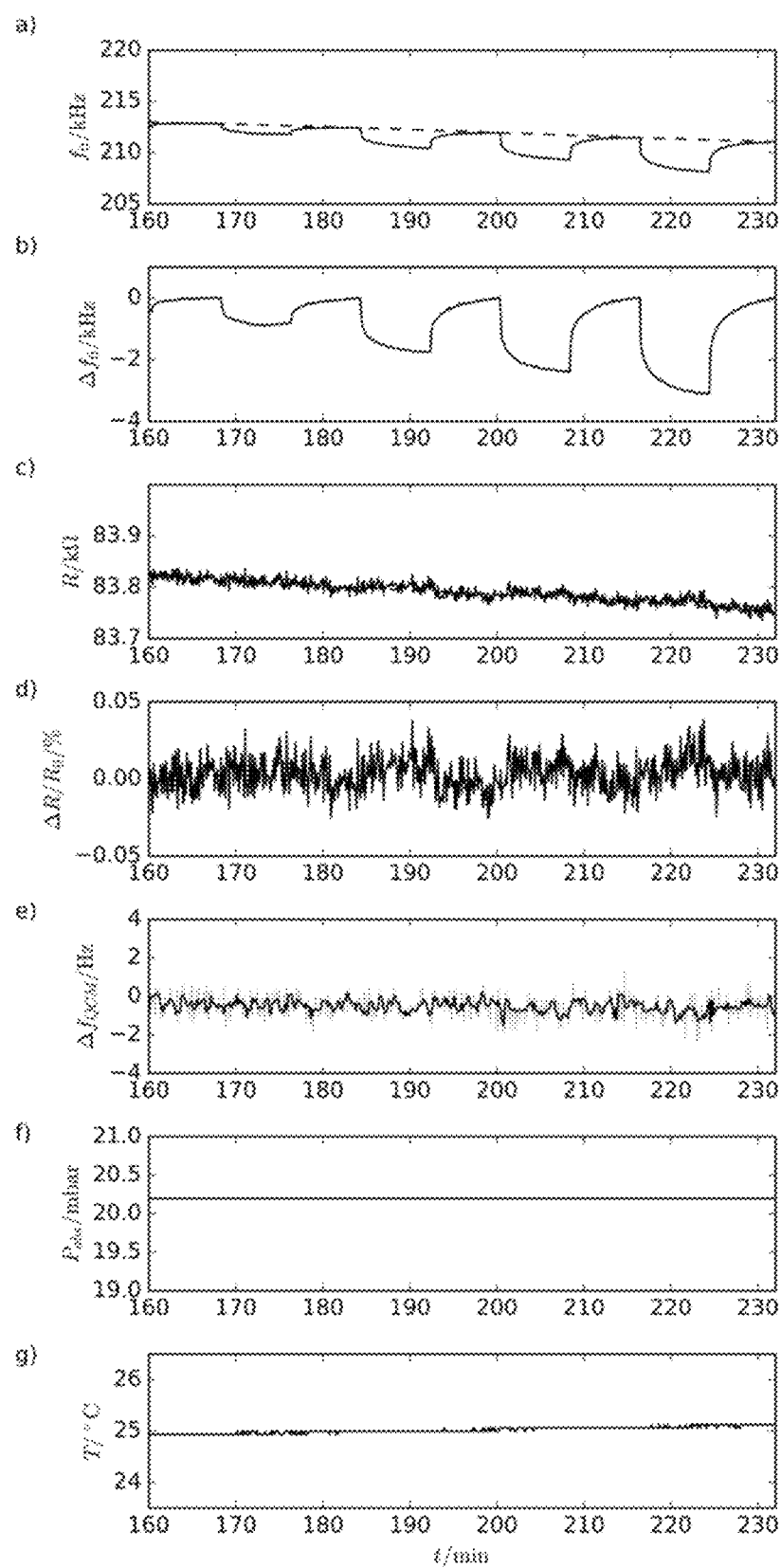

FIG. 11—Time traces showing the fundamental resonance frequency $f_0$ of a chemical sensor according to the invention comprising a freestanding nanoparticle composite material (membrane) under nitrogen gas dosed with 8 min pulses of nitrogen gas enriched with increasing concentrations (partial pressures) of water, i.e. 1000 ppm (2 Pa), 4000 ppm (8 Pa), 7000 ppm (14 Pa), and 10000 ppm (20 Pa) (trace (a)), the corresponding fundamental resonance frequency shift $\Delta f_0$ of the chemical sensor obtained by subtracting the baseline (dashed line in (a)) from $f_0$ (trace (b)), the electrical resistance R of a chemiresistor comprising a nanoparticle composite material (trace (c))—prior art), the corresponding relative electrical resistance change $\Delta R/R_0$ (with $\Delta R=R-R_0$ and $R_0$ being the baseline resistance represented by the dashed line in (c)) (trace (d)—prior art), and the fundamental resonance frequency shift $\Delta f_{QCM}$ of a quartz crystal microbalance coated with a nanoparticle composite material (trace (e)—prior art). Traces (f) and (g) display the total pressure $P_{abs}$ and the temperature T, respectively, measured within the sensor test cell.

Figure 12:
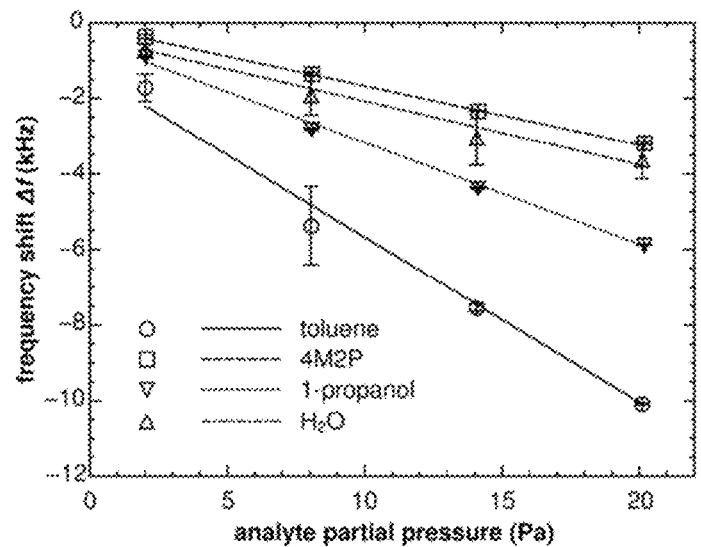

FIG. 12—Calibration curves of chemical sensor CS1 for four different analytes: toluene, 4-methylpentan-2-one (4M2P), 1-propanol, and water ($H_2O$). These curves cover a concentration rage of the analytes corresponding to partial pressures of 2 to 20 Pa at a total pressure of 20 mbar (analytes in nitrogen at room temperature). The curves were obtained by plotting the frequency shift measured after dosing the sensors with the analytes for the duration of 8 minutes at the given partial pressure.

Figure 13:
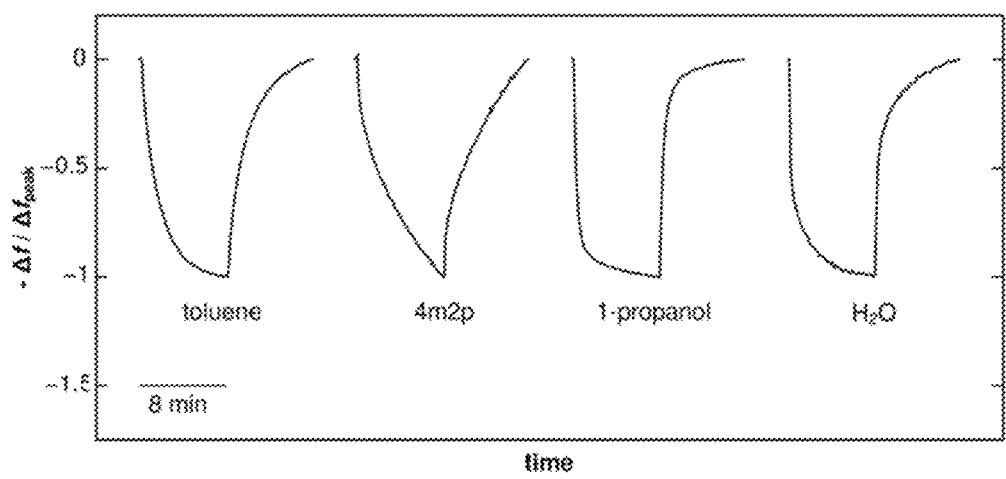

FIG. 13—Normalized, baseline-corrected response transients of chemical sensor CS1 when dosed with different analyte vapors (toluene, 4-methylpentan-2-one (4m2p), 1-propanol, and water ($H_2O$) at a concentration of 10000 ppm (partial pressure: 20 Pa), as indicated. The measurements were conducted at a total absolute pressure of 20 mbar. By comparing the four transient shapes the different response kinetics are clearly recognized. The specific shape of the response transients can be used for recognizing a target analyte. During the experiment the flow of gas/vapor through the sensor cell was kept constant at a rate of ~234 mL FIG. 14—Peak responses of chemical sensor CS1 and a thin film chemiresistor, fabricated from the same gold nanoparticle composite film, after 8 min exposure to 10000 ppm (partial pressure: 20 Pa) of different analyte vapors: toluene, 4-methylpentan-2-one (4m2p), 1-propanol (1prop) and water ($H_2O$). The measurements were conducted at a total absolute pressure of 20 mbar.

DETAILED DESCRIPTION OF THE PRESENT INVENTION

1. Chemical Sensor

The chemical sensor used in the method of the present invention comprises a substrate, optionally one or more insulating layers on at least one side of the substrate, and optionally two or more electrodes.

The term "substrate" as used herein corresponds to the underlying layer, which serves as a foundation for the chemical sensor. Examples of suitable substrates include glass or quartz substrates, indium tin oxide substrates, flexible substrates such as polymers (e.g. polycarbonates, polyimide, polystyrene, polyethylene terephthalate, acrylonitrile butadiene styrene, polymethyl methacrylate, polyolefines, Polyether ether ketone, polyepoxides, SU-8) wafers, such as silicon wafers, in particular thermally oxidized silicon wafers. Preferably, the substrate includes an insulating top layer. In case of a silicon wafer this could be represented by an oxide layer formed by thermal oxidation or chemical vapor deposition, or a silicon nitride layer grown e.g. by chemical vapor deposition.

The "insulating layers" refer to layers of nonconductor material(s), which prevent transfer of electrical charge. In embodiments of the present invention, insulating layers are e.g. employed as supporting layers for composite materials featuring cavities or holes for rendering such materials freestanding. Further, the insulating layers are used for electrical insulation of separate electrodes (e.g. insulation of the top electrode from the bottom electrode). The chemical sensor used in the method of the present invention optionally comprises one or more insulating layers, e.g. 2 or 3 or 4 insulating layers, deposited on at least one side of the substrate. According to one embodiment, the one or more insulating layers can be formed on both sides on the substrate such that the substrate carries a chemical sensor on each side thereof. According to one embodiment, at least one of the one or more insulating layers formed on one side (or both sides) of the substrate is in direct contact with the substrate and/or with at least part of an electrode formed between the substrate and the insulating layer(s).

Spin-coating, dip-coating, roll-coating, spraying, chemical or physical vapor deposition, sputtering, or thermal growth processes belong to the suitable standard coating techniques. In one example the insulating layer is formed by spin-coating. If more than one insulating layer is used, there is no limitation regarding the arrangement of the individual insulating layers relative to each other. According to one embodiment, each individual insulating layer can be made from the same nonconductor material or from different nonconductor materials.

There is no particular limitation as to the nonconductor material which can be used to form the insulating layers. Examples of nonconductor materials are nonconductive polymers, resins, photoresists (positive or negative), polyepoxides, SU-8, inorganic nonconductive materials, such as silicon oxide, silicon nitride, and various metal oxides.

The insulating layers can have a thickness ranging from 5 nm to 1000 µm, preferably from 5 nm to 500 µm, and more preferably from 5 nm to 100 µm.

The electrodes correspond to layers of a material establishing an electrical contact with elements of the chemical sensor. Such layers also form the counter electrodes for applying electrostatic forces to the freestanding nanoparticle composite material, or for establishing a capacitive structure with the freestanding nanoparticle composite, whose capacity can be measured to provide the sensor signal. The chemical sensor used in the method of the present invention comprises two or more electrodes. For instance, the chemical sensor can comprise two electrodes: a back electrode formed between the substrate and the insulating layers, and a top electrode formed on top of the insulating layers. There is however no particular limitation as to the arrangement (place) of the electrodes in the chemical sensor as long as it is technically meaningful, and other arrangements are within the scope of the present invention. The electrodes can be used for controlling and actuating the chemical sensor as well as for interfacing the sensor with external elements such as computation means or the like.

The electrodes are formed of an electrically conductive material, which are well-known in the art. Suitable materials for the electrodes include metals such as titanium, chromium, aluminum, magnesium, copper, nickel, noble metals such as gold, silver, palladium, platinum and alloys thereof, conductive oxides such as indium tin oxides, carbon based materials such as carbon black and graphene or reduced graphene oxide and carbon nanotubes. The electrodes can be fabricated using standard photolithography based etching and deposition processes as described in the examples. To achieve better adhesion to the underlying substrates, layered electrodes can be deposited, e.g. Ti/Au or Cr/Au electrodes.

Further, contact printing or ink-based processes such as ink jet printing of inks containing metal or carbon-based particles can be used for electrode deposition.

The electrodes can have a thickness ranging from 5 nm to 100 µm, preferably from 5 nm to 10 µm, and more preferably of from 5 nm to 1 µm.

According to one preferred embodiment, the substrate and/or insulating layers comprise one or more microcavity, i.e. one microcavity or a plurality of microcavities, onto which a freestanding nanoparticle composite material is suspended.

The term "microcavity" refers to a hollow and unfilled space formed in the substrate and/or insulating layers. The microcavity can have any shape, as long as it is suited for preparing a freely suspended nanoparticle composite material. According to one embodiment, the microcavity or microcavities have a cylindrical (thus forming circular apertures), square, (thus forming square apertures), or rectangular (rectangular apertures) shape.

The depth of the cavity in the substrate and/or in the insulating layer can be in the range from 10 nm to 1000 µm, preferably from 10 nm to 500 µm, more preferably from 10 nm to 100 µm. However, the cavity can also be a hole through the whole thickness of substrate supporting the nanoparticle composite.

According to one embodiment, the microcavity defines a cylindrical hollowed-out space in the thickness of the insulating layer(s), having a diameter ranging from 100 nm to 5000 µm, preferably from 100 nm to 1000 µm, and more preferably from 100 nm to 500 µm (the height being defined as the thickness of the insulating layer(s)).

According to one further embodiment, the microcavity defines a square-shaped (cuboid) hollowed-out space in the thickness of the insulating layer(s) having an edge length of 100 nm to 5000 µm, preferably of 100 nm to 1000 µm, and more preferably of 100 nm to 500 µm (the height being defined as the thickness of the insulating layer(s)).

A typical chemical sensor which can be used in the method according to the present invention is depicted in FIG. 3, which shows a chemical sensor comprising a substrate (4), an insulating layer (5) comprising a microcavity (6), e.g. a cylindrical microcavity, two electrodes (7): a back electrode formed at the bottom of the microcavity and a top electrode formed on top of insulating layer (5), e.g. concentrically around the edge of the upper cavity opening, and a freestanding nanoparticle composite material (3), e.g. a membrane, which is suspended over the microcavity (6).

The chemical sensor can be combined with other chemical sensors to form a sensor array, which can be used as e.g. an electronic nose. For example, several chemical sensors can be fabricated using different freestanding nanoparticle composite materials (e.g. different nanoparticles, matrix, thickness, geometries etc.) so as to provide an array comprising multiple sensors, each sensor having a different chemical selectivity. Exposing a sensor array to an analyte produces a specific signal pattern for that analyte and thus, allows recognizing the analyte, i.e. distinguishing a target analyte from other compounds. The signal pattern allowing the recognition of an analyte can also be associated with the specific response kinetics of the individual sensors.

2. Freestanding Nanoparticle Composite Material

The chemical sensor used in the method of the present invention comprises a freestanding nanoparticle composite material. Such freestanding material is, for example, formed when a nanoparticle composite film is partly detached from a substrate (or from an insulating layer on the substrate). The detached parts of the film are freestanding (self-supported), meaning that they are connected to the substrate (or the insulating layer on the substrate) only indirectly via the directly supported parts of the film (i.e. via the parts of the film which are in direct contact with the substrate or the insulating layer on the substrate). Such detached part of a nanoparticle film can, e.g., form a cantilever protruding away from the substrate surface, e.g., from the edge of the substrate.

Preferably, the freestanding nanoparticle composite is suspended onto at least a part of the microcavity or microcavities mentioned above. The composite material forms a permeable network of nanoparticles allowing for the sorption (adsorption and/or absorption) and/or diffusion of the analyte species therein. Accordingly, when the freestanding nanoparticle composite material is exposed to an analyte (e.g. an analyte contained in the gas phase), the analyte can be sorbed within and on the surface of the composite material, and/or bind to and/or interact with the surface of the nanoparticles (adsorption), and/or be absorbed within the nanoparticles.

The sorption of an analyte within the composite material and/or at the nanoparticles' surface affects inter- and/or intramolecular interactions (e.g. hydrogen bonding, ionic, dipolar, induced dipolar, covalent, coordinative, pi-pi interactions) between the constituents of the composite material, leading to softening or stiffening (i.e. a change in the elastic modulus and/or pre-stress) or a change in strain, resulting in variations of the pre-stress of the composite material. Moreover, the sorption of an analyte within the nanoparticles can cause a volume increase (swelling), which can also affect the pre-stress of the nanoparticle composite material, e.g. decrease the tension or increase the compression of the composite material.

The term "suspended" as used herein means that the freestanding nanoparticle composite material is hung or spanned freely onto the microcavity except at the point(s) of support.

Figure 4:
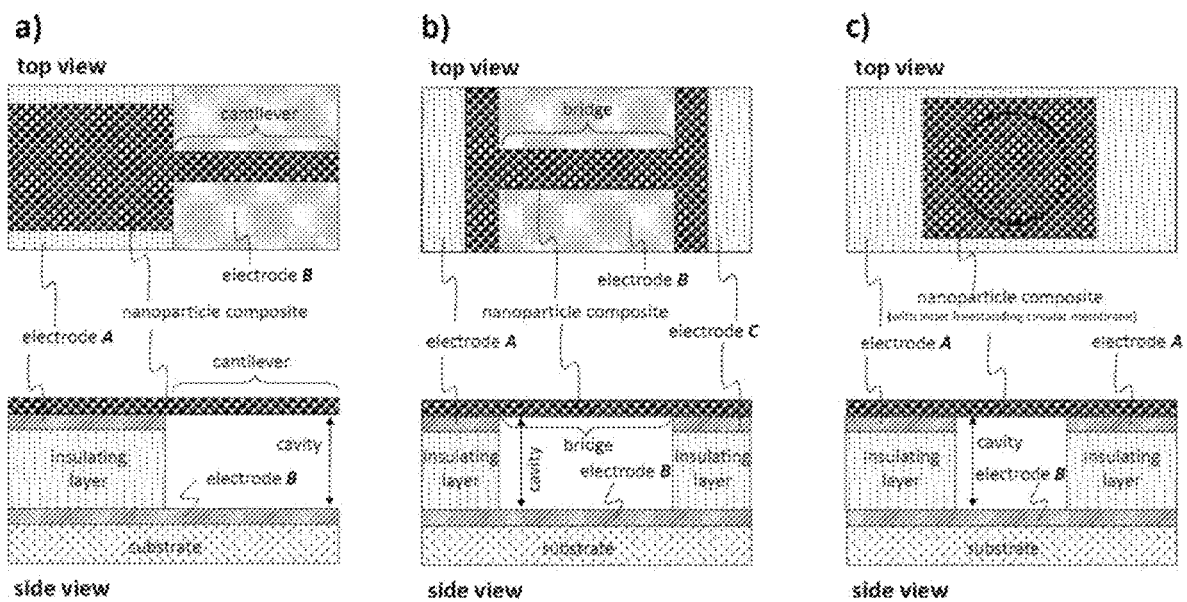

The freestanding nanoparticle composite material, which is permeable to the analyte, can have various geometries. For example, it can form a cantilever, or it can form a freestanding membrane, which can completely cover the microcavity, or which can cover only a part or parts of the microcavity (e.g. by forming a bridge). For illustration, three examples are provided in FIG. 4, showing (a) a nanoparticle composite material forming a freestanding cantilever thus covering only a part of the microcavity, (b) a nanoparticle composite material forming a freestanding bridge (i.e. doubly-clamped membrane or beam) thus covering only a part of the microcavity, and (c) a nanoparticle composite material forming a freestanding membrane that covers the microcavity completely. These examples are meant solely to illustrate some aspects of the chemical sensor used in the present invention without limiting the scope of the present invention.

According to one embodiment, the freestanding nanoparticle composite material is suspended onto at least a part of the microcavity or microcavities as a cantilever, a single- or multiple-clamped-beam, a string, a plate, or a membrane (thin film).

According to one preferred embodiment, the freestanding nanoparticle composite material is suspended onto the microcavity or microcavities as a membrane, the said membrane preferably having a thickness lower than 1000 nm, more preferably lower than 500 nm, more preferably lower than 200 nm.

The thickness of a substrate-supported nanoparticle composite material (e.g. before transferring it onto a cavity to form the freestanding nanoparticle composite) can be determined by atomic force microscopy (AFM) as described by Schlicke et al. in *Nanotechnology* 2011, 22, 305303.

According to one embodiment, the freestanding nanoparticle composite material, e.g. arranged as a freestanding membrane, is under tension and has a positive pre-stress (also termed residual stress).

Further, the nanoparticles forming the freestanding nanoparticle composite material can be arranged as ordered mono-, bi- or multilayer structures as described by He et al. in *Small* 2010, 6, 1449-1456 and Kanjanaboos et al. in *Nano Lett.* 2013, 13, 2158-2162. The nanoparticles forming the freestanding nanoparticle composite material can also be arranged in a disordered manner as described by Schlicke et al. in *Nanotechnology* 2011, 22, 305303.

The nanoparticle composite material, e.g. a membrane of nanoparticle composite material, can be fabricated by standard techniques, such as dip-coating, spray-coating, drop casting, convective self-assembly, ink-jet printing, self-assembly (including layer-by-layer self-assembly), Langmuir-Blodgett technique, or a spin-coating technique as described by Schlicke et al. in *Nanotechnology* 2011, 22, 305303. According to the spin-coating method, a solution of nanoparticles, e.g. ligand-capped nanoparticles, and a solution of the matrix (if any), e.g. molecular cross-linkers, are applied alternatingly onto a rotating substrate, e.g. a glass slide. Afterwards, the coated glass slide is floated on demineralized water, and after several days, the membrane can be detached by carefully immersing the substrate into the aqueous phase, leaving the membrane of nanoparticle composite material free-floating at the liquid-air interface. The floating membrane can be skimmed using a lithographically structured substrate which, at this manufacturing step, comprises e.g. the three-dimensional electrode microstructure (i.e. the substrate and optional insulating layers/electrodes comprising one or more microcavities). The obtained chemical sensor, comprising the nanoparticle film covering at least parts of the microcavity or microcavities, can then be dried, and eventually mounted onto a printed circuit board. Alternatively, the spin-coated nanoparticle film can also be transferred onto the lithographically structured substrate via contact printing to form the chemical sensor comprising the freestanding nanoparticle composite.

2.1 Nanoparticles

The freestanding nanoparticle composite material comprises nanoparticles. The term "nanoparticles" refers to small particles of various shapes having a maximum size in at least one dimension confined between the length corresponding to the thickness of a monolayer of atoms (e.g. graphene, $MoS_2$) and several 100 nm. There are known nanoparticles having about the same size in all three dimensions in space as well as nanowires, nanofibers, and nanotubes having a larger size in one dimension in space, and nanosheets having a larger size in two dimensions in space. All those nanoparticles can be used in the assembly of the chemical sensor used in the method of the present invention.

According to one embodiment, the nanoparticles are spherical, polyhedral, star-shaped or elongated e.g. rod-, tube- or fiber-shaped, plate or sheet-like, and preferably have in at least one dimension a length lower than 100 nm, more preferably lower than 50 nm, and more preferably lower than 30 nm.

According to one preferred embodiment, the nanoparticles are essentially spherical particles (thus having about the same size in all three dimensions in space) having an average diameter lower than 100 nm, preferably lower than 50 nm, more preferably lower than 30 nm. "Essentially spherical particles" have a spheroidal or ellipsoidal geometry, with the latter having an aspect ratio of the long axis to the short axis of 1-2. However, it is to note that crystalline nanoparticles tend to form facetted surfaces, with the facets of lower surface energies being more abounded than those of higher surface energies. Thus, for someone skilled in the art, it is obvious that the term "essentially spherical particles" includes nanoparticles which can deviate somewhat from the perfect geometry of a sphere or ellipsoid due to the formation of such facetted surfaces.

According to one further preferred embodiment, the nanoparticles are polyhedral particles having a length in at least one dimension lower than 100 nm, preferably lower than 50 nm, more preferably lower than 30 nm.

The nanoparticles can be characterized by using techniques known in the art such as e.g. transmission electron microscopy (TEM), dynamic light scattering (DLS), UV/Vis- and fluorescence spectroscopy.

The nanoparticles used in the freestanding nanoparticle composite material according to the present invention can be formed of: (a) a metal, in particular a noble metal such as Au, Pt, Ag, Pd, a coinage metal such as Cu, Ni, Co, Mn, Fe, and alloys thereof; (b) a metal oxide such as iron oxides (e.g. $Fe_3O_4$, $Fe_2O_3$), $SnO_2$, $TiO_2$, and indium tin oxides; (c) a semiconductor, in particular a II/VI semiconductor such as CdS, CdSe, CdTe, ZnS, ZnSe, ZnTe, HgS, HgSe, HgTe, and/or a III/V semiconductor such as GaAs, InP; (d) carbon such as carbon black, carbon nanotubes, graphite, a mono- or multilayered two-dimensional carbon material such as flakes of graphene, graphene oxide, or reduced graphene oxide; (e) a metal chalcogenide, in particular a transition metal chalcogenide, a mono- or multilayered two-dimensional metal chalcogenide material such as flakes of a transition metal chalcogenide, such as $MoS_2$ sheets; or any combination of these materials so as to form, for instance, core-shell, core-shell-shell, or Janus-type nanoparticles (i.e. nanoparticles whose core/shell(s) are formed of different materials or nanoparticles whose outer surface and/or volume fractions are formed of two or more different materials). The freestanding nanoparticle composite material can also comprise any combinations (different kinds) of nanoparticles formed from the materials hereinabove mentioned.

According to one preferred embodiment, the freestanding nanoparticle composite material comprises nanoparticles formed of a noble metal such as Au, Pt, Ag, Pd, preferably Au, i.e. gold nanoparticles (GNPs).

The synthesis of nanoparticles is well-known in the art. The gold nanoparticles as used herein can e.g. be synthesized according to the procedure described by Leff et al. in *Langmuir* 1996, 12, 4723-4730. The synthesized nanoparticles are stabilized (capped) by ligands which were added to the reaction mixture used for their synthesis. These original ligands may be replaced later by other ligands and/or cross-linkers to form the nanoparticle composite material. Suitable ligands for capping the nanoparticles (e.g. GNPs) include among many examples organic amines, thiols, thiocarbamtes, dithiocarbamtes, isocyanides, carboxylic acids, dihydroxyphenyl derivatives, phosphines, phosphine oxides, phosphonic acids, halogenides, or other ionic compounds.

2.2 Matrix

The freestanding nanoparticle composite material can comprise a matrix in which the nanoparticles are dispersed and/or interconnected with each other. The term "matrix" as used herein refers to a material in which the nanoparticles are embedded. The term "dispersed" as used herein means that the nanoparticles are distributed within the matrix. The term "interconnected" as used herein means that each nanoparticle is connected (linked) to at least one other nanoparticle, preferably more nanoparticles, so as to form a network of nanoparticles. The interactions interconnecting the particles can include any kind non-covalent interactions as well as the formation of covalent bonds.

According to one embodiment of the present invention, the matrix comprises a material selected from the group consisting of: (A) organic polymers; (B) polysiloxanes; (C) organic ligands, in particular mono-, bi- or polyfunctional organic ligands that are able to attach to the surface of the nanoparticles with at least one functional group, such functional group(s) preferably being selected from the groups comprising sulfur-containing functionality, or nitrogen-containing functionality, or phosphorus-containing functionality, or oxygen-containing functionality; (D) organic cross-linkers, in particular bi- or polyfunctional organic cross-linkers that are able to attach to the surface of the nanoparticles with at least two functional groups, such functional groups preferably being selected from the groups comprising sulfur-containing functionality, or nitrogen-containing functionality, or phosphorus-containing functionality, or oxygen-containing functionality; and combinations of these materials.

According to one further embodiment, the matrix is attached to the surface of the nanoparticles via covalent bonds, ionic bonds, coordinative covalent (dipolar) bonds and/or multiple dipolar interactions. Preferably, the matrix is attached to the surface of the nanoparticles via carbon-to-nanoparticle bonds such as carbon-to-metal bonds or carbon-carbon bonds, or via one or more functional groups, such functional group(s) preferably being selected from thiol, disulfide, carbamate, thiocarbamate, dithiocarbamate, amino, carboxylic acid, hydroxyl, polyether, isocyanide, dihydroxyphenyl, phosphine, phosphine oxide, phosphonic acid groups.

According to one preferred embodiment, the nanoparticles are cross-linked with a bi- or polyfunctional organic cross-linker having functional groups that are able to attach (bind) to the surface of the nanoparticles such as thiol, disulfide, amino, carboxylic acid, hydroxyl, isocyanide, dihydroxyphenyl, phosphine, phosphine oxide, and phosphonic acid groups. Examples of suitable cross-linkers which can be used in the present invention are described in EP 1 215 485 B1, which is incorporated therein by reference.

According to one more preferred embodiment, the nanoparticles, especially metal nanoparticles, such as Au, Ag, Pt, Pd, and Pt/Co or Pt/Ni alloy nanoparticles, are cross-linked using linear or branched bifunctional or polyfunctional cross-linkers having thiol groups, dithiocarbamate groups, disulfide groups, or amino groups, such as $\alpha,\omega$-alkanedithiols, thiol or disulfide polyfunctionalized oligomers, polymers, and dendrimers, or amine polyfunctionalized oligomers, polymers, or dendrimers, e.g. poly(amidoamine) (PAMAM) dendrimers.

3. Method for Detecting an Analyte with a Chemical Sensor Comprising a Freestanding Nanoparticle Composite Material The method for detecting an analyte according to the present invention comprises the steps of:

(i) exposing a chemical sensor comprising a freestanding nanoparticle composite material as hereinabove described to an analyte; and (ii) measuring a sensor signal that is caused by a change of the elastic modulus and/or pre-stress of the freestanding nanoparticle composite material by a detection means.

The term "analyte" as used herein refers to any compound or chemical entity of interest. The analyte can be in a fluid phase. Preferably, the analyte is present in the gas phase.

As hereinbefore mentioned, a change of the elastic modulus and/or pre-stress of the composite material can occur when an analyte is sorbed within and on the composite material, and/or binds to and/or interacts with the surface of the nanoparticles, and/or is absorbed within the nanoparticles. The sensor signal that is caused by a change of the elastic modulus and/or pre-stress of the freestanding nanoparticle composite material corresponds to any measurable change of a physical property associated with the chemical sensor comprising the freestanding nanoparticle composite material and/or the freestanding nanoparticle composite material itself, e.g. a change of electrical resistance/impedance, capacitance, or magnetic field, or a change of light scattered by, or reflected from, or emitted from the freestanding nanoparticle composite.

The interaction of an analyte with the nanoparticle composite material can be reversible or irreversible, enabling a reversible or irreversible sensor signal. Examples for reversible interactions include the reversible physisorption of solvent molecules on and within the composite material. Examples of irreversible interactions include chemisorption involving the formation of strong chemical bonds between the analyte and the composite material, e.g. between the analyte and the matrix and/or the nanoparticles' surfaces. For instance, thiols are known to bind virtually irreversibly to the surface of gold nanoparticles by the formation of covalent bonds.

Without being bound to theory, it is believed that the change in pre-stress/and or elastic modulus is caused by swelling or compression (corresponding to a change in strain) of the composite material and/or by breaking/weakening or formation/strengthening of chemical bonds/interactions within the matrix or between the matrix and the nanoparticles. For example, many volatile organic compounds, such as toluene, are physisorbed reversibly within a hydrophobic organic matrix and, thus, cause reversible swelling of the matrix. This swelling (corresponding to a reduction in strain) reduces the pre-stress of the material. However, if the analyte is e.g. a thiol and the composite material comprises gold nanoparticles, the analyte is chemisorbed at the gold surface. As a consequence, such chemisorption of the analyte can replace functional groups of the matrix previously attached to nanoparticles and the degree of crosslinking will be diminished, i.e. the composite material will become less stiff (lowering of the elastic modulus).

By "detection means", we understand any device or equipment which can be used to detect and/or measure (e.g. optically, electrically, magnetically) a change of a physical property associated with the chemical sensor and/or the freestanding nanoparticle composite material.

According to one embodiment, the sensor signal that is caused by a change of elastic modulus and/or pre-stress of the freestanding nanoparticle composite material is detected by optically measuring a change in the structure and/or topography, and/or shape, and/or size of the composite material (optical detection mode). For instance, if the change of the elastic modulus and/or pre-stress affects the structure and/or topography, shape or geometric dimensions of the freestanding nanoparticle composite, such change can be detected by optical means, e.g. by the detection of light reflected from the surface of the freestanding composite material and/or scattered by and/or emitted from the nanoparticle composite material.

According to further embodiments, the sensor signal can also be detected by measuring a change of the electrical resistance/impedance of the composite material, by measuring a change of the capacitance of the composite material arranged with one or more proximate electrodes, and/or by measuring the magnetic field in proximity of the composite material.

Optical detection can include the measurement of the intensity of light reflected from or scattered by the composite material and can also involve the analysis of phase information. The light source can be a laser, a laser diode, a light emitting device, but is not limited to these examples. Furthermore, the device used for detecting the light reflected from or scattered by the composite material can be a photodetector, a position sensitive photodetector, a four- or multi-plate photodetector, a camera, a CCD/CMOS camera, a CCD/CMOS chip, an interferometer, a microscope, but is not limited to these examples.

If the nanoparticle composite material comprises photo- or electroluminescent nanoparticles e.g. semiconductor particles, it is possible to excite their luminescence and use any change of light emitted from the particles to detect a change of the composite material's elastic modulus and/or pre-stress by measuring any resulting change of topography, shape, size, and structure. In principle, the same light sources and detection systems as mentioned above for the detection of light reflected from or scattered by the freestanding nanoparticle composite material can be used.

Preferably, the change in the structure and/or topography, shape, or size of the composite material is detected by detecting light reflected and/or emitted from and/or scattered by the composite material.

The chemical sensor comprising a freestanding nanoparticle composite material and/or the detection system can be part of a hand-held electronic device such as a mobile phone e.g. involving the camera and a light source of the mobile phone, or can be attached in any functional manner to the mobile phone.

The change of the elastic modulus and/or pre-stress of the freestanding nanoparticle composite material can also be probed by actuating the nanoparticle composite material by applying a force and monitoring the composite material's response.

Actuation can be performed, for example, by using a piezoelectric actuator, by deflecting or indenting the nanoparticle composite material using a cantilever, by thermal excitation, by laser pulses, or by magnetic fields. If the nanoparticle composite comprises conductive nanoparticles, providing the material with sufficient electric conductivity, the freestanding nanoparticle composite can be actuated by applying a DC or AC electric field, i.e. by electrically charging the freestanding nanocomposite material against a counter electrode as described by Schlicke et al. in *ACS Appl. Mater. Interfaces* 2015, 7, 15123-15128 and *Nanoscale* 2016, 8, 15880-15887. Actuation of the freestanding nanoparticle composite material can be performed in a quasi-static manner (quasi-static mode) (Schlicke et al., *ACS Appl. Mater. Interfaces* 2015, 7, 15123-15128) or in a dynamic manner (dynamic mode) (Schlicke et al., *Nanoscale* 2016, 8, 15880-15887).

According to one embodiment, the sensor signal that is caused by a change of elastic modulus and/or pre-stress of the freestanding nanoparticle composite material is detected by:

applying a quasi-static actuating force (quasi-static mode) on the composite material, such as an electrostatic force, a piezoelectric force, or a magnetic force; and by measuring the response of the composite material to the actuating force.

According to one other embodiment, the sensor signal that is caused by a change of elastic modulus and/or pre-stress of the freestanding nanoparticle composite material is detected by:

applying a dynamic actuating force (dynamic mode), such as a dynamic electrostatic force e.g. an electrostatic force induced by an alternating (AC) electric field preferably having a frequency between 1 kHz to 10 GHz, or a magnetic force, e.g. induced by an alternating magnetic field, or a photon-induced force, e.g. imposed by an incident pulsed laser beam, or a force caused by a piezoelectric actuator driven by an AC voltage, such that the composite material oscillates at one of its resonance frequencies; and by measuring a shift of the resonance frequency, and/or any change in amplitude and/or phase of the freestanding nanoparticle composite at a given drive frequency.

When actuating the freestanding composite material in the dynamic mode, the chemical sensor is preferably operated as a resonator, meaning that the freestanding nanoparticle composite material oscillates with a frequency at its fundamental mode or at higher order mode frequencies. In the context of the present invention, the expression "a frequency at its fundamental mode or at higher order mode frequencies" encompasses the fundamental or higher order mode resonance frequencies, and also frequencies that are close to the fundamental or higher order mode resonance frequency, i.e. the frequency range centered at a resonance frequency and limited by the frequencies at which the oscillation amplitude decays to the noise level of the amplitude spectrum.

According to one further embodiment, the quasi-static actuation mode and/or dynamic actuation mode can be combined with each other and with other non-actuated detection modes (multi-mode). That is, the sensor signal that is caused by a change of elastic modulus and/or pre-stress of the freestanding nanoparticle composite material is detected by:

measuring as the sensor signal a change of a physical property which can be detected without applying an actuating force e.g. a change of an electrical property such as resistance/impedance, and/or a change of an optical property such as spectral absorbance, emission, and/or reflectance; and/or by measuring as the sensor signal a change of the composite material's response to a quasi-static actuating force, and/or a dynamic actuating force.

($\alpha$) The response of the freestanding nanoparticle composite material to an actuating force (a quasi-static and/or dynamic actuating force), i.e. its deflection and movement, can be monitored by optical means. For example, light reflected or emitted from the composite material, or scattered by the composite material, can be detected using e.g. a position sensitive photo detector, an interferometer, a confocal microscope, a CCD/CMOS camera, etc. Alternatively, the movement of the freestanding nanoparticle composite can be monitored by a cantilever probe, as used for example in atomic force microscopes.

($\beta$) If the freestanding nanoparticle composite material comprises electrically conductive nanoparticles, its strain sensitive electrical resistance/impedance can be used to monitor any variations in its deflection/movement behavior, caused by a change of the elastic modulus and/or pre-stress of the composite material.

(γ) The freestanding nanoparticle composite material can be arranged with a counter electrode to form a capacitor. A change in the material's position can then be detected by monitoring the capacitance of this arrangement.

(δ) Further, if the freestanding nanoparticle composite material comprises magnetic particles, movement of the freestanding composite can be detected by measuring any change of the magnetic field in the composite material's proximity.

The change in the composite material's elastic modulus and/or pre-stress can also be detected by deflecting the material by applying a quasi-static force and measuring the amplitude of the deflection. A change in the composite material's elastic modulus and/or pre-stress caused by sorption of an analyte can result in a measurable change of the freestanding nanoparticle composite material's deflection when applying the same force continuously or repeatedly. This mode for detecting a change in the mechanical properties of the freestanding nanocomposite caused by analyte sorption is preferably used when applying the sensor at ambient pressure, but can also be used when applying the sensor under reduced pressure.

4. Method for Determining the Concentration of and/or for Recognizing an Analyte According to one embodiment, the method of the present invention can be used for determining the concentration of an analyte, the method comprising the consecutive steps of:

(1) calibrating a chemical sensor as hereinabove described by measuring a sensor signal that is caused by a change of the elastic modulus and/or pre-stress of the freestanding nanoparticle composite material by a detection means when exposing the chemical sensor to a reference sample of an analyte, e.g. an analyte in the gas phase, at various known concentrations (step (iii));

(2) exposing the chemical sensor to a test sample containing an analyte at unknown concentration (step (i));

(3) measuring the sensor signal that is caused by a change of the elastic modulus and/or pre-stress of the freestanding nanoparticle composite material by a detection means (step (ii)); and (4) comparing the sensor signal measured by exposing the chemical sensor to a test sample of the analyte to the calibration data measured in (1) in order to determine the concentration of analyte in the test sample (step (vi)).

The calibration data mentioned above can be readily obtained by exposing the chemical sensor comprising a freestanding nanoparticle composite material to a reference sample of an analyte at various known concentrations. FIG. 12 shows examples of calibration curves—i.e. the fundamental vibrational resonance frequency shift optically measured as a function of the partial pressure (concentration) of an analyte—obtained for four analytes: toluene, 4-methylpentan-2-one, 1-propanol and water. As can be seen in FIG. 12, there is a linear relationship between the partial pressure (concentration) of the analyte and the observed frequency shift. As a result, when the chemical sensor is exposed to a test sample of an analyte, the concentration of the analyte in the test sample can be easily determined by comparing the measured frequency shift with the calibration data. If the analyte in the test sample is present at a concentration outside the range of concentration used for calibrating the chemical sensor, the concentration of the analyte in the test sample can be approximated by extrapolation from the calibration data or determined after expanding the concentration range for the calibration procedure.

According to one further embodiment, the method of the present invention can be used for recognizing an analyte, the method comprising the consecutive steps of:

(1) optionally adjusting the chemical selectivity of the freestanding nanoparticle composite material of a chemical sensor as, described below, to an analyte to be recognized (step (v));

(2) calibrating the chemical sensor by measuring the sensor signal when exposing the chemical sensor to a reference sample of a known analyte (step (vi));

(3) exposing the chemical sensor to a test sample containing an (unknown) analyte (step (i));

(4) measuring the sensor signal that is caused by a change of the elastic modulus and/or pre-stress of the freestanding nanoparticle composite material by a detection means (step (ii)); and (5) comparing the sensor signal, such as the signal shape (response kinetic), measured by exposing the chemical sensor to a test sample of an analyte, to the calibration data measured in (2) in order to recognize the analyte in the test sample (step (vii)).

The method herein described can be used to recognize an analyte by comparing the sensor signal to calibration data measured by exposing the chemical sensor to a reference (calibration signal) step. This embodiment is also based on the principle that the freestanding nanoparticle composite material can exhibit different response kinetics for different analytes. The response kinetic can be characteristic for an analyte, thus enabling recognizing a target analyte, e.g. an analyte in the gas phase.

FIG. 13 shows the sensor signal (i.e. the resonance frequency shift) of a freestanding nanoparticle composite (membrane) measured for four different analytes—i.e. toluene, 4-methylpentan-2-one, 1-propanol and water—at a concentration of 10000 ppm (partial pressure: 20 Pa). As can be seen in FIG. 13, the chemical sensor exhibits different response kinetics (e.g. transient shapes) for different analytes. The specific shape of the signal response, which is characteristic for an analyte of interest, can be used for recognizing that analyte.

Furthermore, the embodiments hereinbefore described can be combined. That is, the method of the present invention can be used for recognizing an analyte and for determining its concentration at the same time.

The chemical selectivity of the freestanding nanoparticle composite material can be adjusted/tuned such that the chemical sensor is suited for recognizing a specific (target) analyte or a class of analytes (e.g. non-polar, hydrophobic analytes or polar, hydrophilic analytes). The chemical selectivity of the composite material can be adjusted by changing the chemical composition of the freestanding nanoparticle composite material as described e.g. in EP 1 215 485 B1 and e.g. by Olichwer et al. in *ACS Appl. Mater. Interfaces* 2012, 4, 6151-6161.

For example, if the matrix containing the nanoparticles is hydrophilic/polar, the composite material will preferably sorb hydrophilic and/or polar analytes and thus, the sensitivity of the chemical sensor will be higher for such hydrophilic, polar analytes than for hydrophobic, non-polar analytes. Conversely, if the matrix is hydrophobic and/or non-polar, the composite material will preferably sorb hydrophobic/non-polar analytes and thus, the sensitivity of the chemical sensor will be enhanced for hydrophobic analytes. In another example, the matrix can be functionalized with groups acting as hydrogen bond acceptors/donors. This allows enhancing sorption of analytes which are hydrogen bond donors/acceptors and thus, the sensitivity of the chemical sensor for such analytes can be enhanced.

Also, the chemical nature of the nanoparticles can be used to adjust/tune chemical selectivity. If the freestanding nanoparticle composite material is formed using e.g. gold, silver, or platinum nanoparticles, it will interact strongly with sulfur-containing analytes (e.g. thiols, $H_2S$, $CS_2$) or with amines, $NH_3$, and CO, because such compounds bind tightly to the metal surfaces, as described e.g. by Briglin et al. in *Langmuir* 2004, 20, 299-305 and Joseph et al. in *Sens. Actuators B* 2004, 98, 188-195. As a result, chemical sensors comprising such nanoparticles within the freestanding composite material are expected to exhibit enhanced sensitivity for sulfur-containing analytes, amines, $NH_3$ and CO. Furthermore, the use of a freestanding nanoparticle composite material comprising palladium nanoparticles allows enhancing the sensitivity of the chemical sensor to hydrogen gas, due to the ability of palladium to sorb hydrogen, thus causing an increase of the nanoparticle's volume.

In addition, the chemical selectivity of the freestanding nanoparticle composite material can be adjusted by modifying the permeability of the composite material, e.g. by modifying the structure of the cross-linker(s) (e.g. length and/or chemical nature) used to interconnect the nanoparticles in the same manner as described in U.S. Pat. No. 6,458,327 which is herein incorporated by reference. These modifications allow changing the size of the pores and pathways which are available for the analyte to penetrate the composite material and to be sorbed therein. As a result, a chemical sensor having a size selective sensitivity can be achieved. Moreover, when using a polymer as the matrix binding/interconnecting the nanoparticles, chemical selectivity can be achieved via molecular imprinting, as described by Holthoff et al. in *Anal. Chim. Acta* 2007, 594, 147-161.

According to one embodiment, the chemical sensor can be combined with other chemical sensors to form a sensor array, which can be used as e.g. an electronic nose. For example, several chemical sensors can be fabricated using different freestanding nanoparticle composite materials (e.g. different nanoparticles, matrix, thickness, geometries etc.) so as to provide an array comprising multiple sensors, each sensor having a different chemical selectivity. Exposing a sensor array to an analyte produces a specific signal pattern for that analyte and thus, allows recognizing the analyte, i.e. distinguishing a target analyte from other compounds. The signal pattern allowing the recognition of an analyte can also be associated with the specific response kinetic of one, a fraction, or all chemical sensors forming the sensor array.

According to one further embodiment, the chemical sensor comprising a permeable freestanding nanoparticle composite material or an array of such chemical sensors can be combined with at least one other chemical and/or physical sensor having a different chemical selectivity and/or a different signal transduction mechanism, such as a QCM or a chemiresistor, in order to produce a signal pattern that allows the recognition of a target analyte, and to detect physical properties, such as pressure and temperature.

Figure 14:
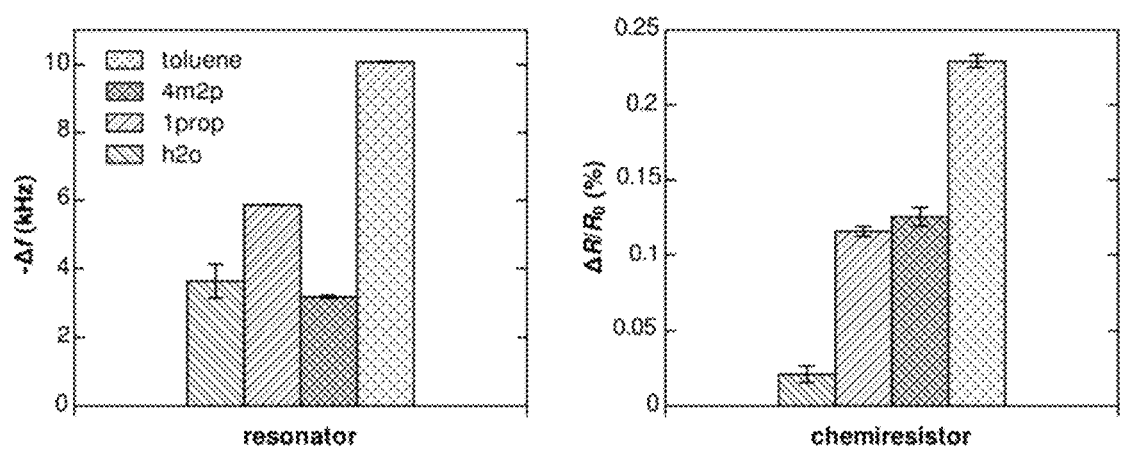

FIG. 14 shows the responses of a chemical sensor comprising a freestanding nanoparticle composite material (left) and a chemiresistor (right) formed of the same nanoparticle composite material to four different analytes—i.e. toluene, 4-methylpentan-2-one, 1-propanol and water—at a concentration of 10000 ppm (partial pressure: 20 Pa). As can be seen in FIG. 14, different signal transduction mechanisms produce different signal intensities for different analytes. This information can be used for recognizing a target analyte.

5. Examples

The following sensors and test methods were used to evaluate the method of the present invention.

5.1 Synthesis of Gold Nanoparticles

Different batches of 1-dodecylamine capped gold nanoparticles (GNPs) were used for the fabrication of freestanding nanoparticle composites (membranes) in the examples of the present invention. All the GNP batches were synthesized according to the procedure described by Leff et al. (cf. *Langmuir* 1996, vol. 12, pages 4723-4730). The obtained GNPs were characterized using UV/vis spectroscopy and transmission electron microscopy (TEM). As observed earlier by Schlicke et al. (cf. *Nanotechnology* 2011, 22, 305303), the dodecylamine-capped GNPs were not stable under TEM conditions. Therefore, the GNPs were stabilized for the TEM measurements by exchanging the dodecylamine ligands with 1-dodecanethiol ligands before conducting TEM measurements.

Average particle sizes were estimated by measuring the projected area of hundreds of particles imaged via TEM. Assuming spherical shapes of the particles, particle diameters were computed from the respective areas and averaged. Particles with diameters of <1 nm were excluded from sizing statistics. Particles with average diameters in the range of 3 to 4 nm and with relative size dispersity (standard deviations) typically between 10 to 30% were used for the fabrication of cross-linked gold nanoparticle films (see TEM images shown in FIG. 1).

5.2 Preparation of Cross-Linked GNP Films 1,6-hexanedithiol (6DT) cross-linked GNP films were fabricated according to a procedure similar to that described by Schlicke et al. in *Nanotechnology* 2011, 22, 305303. The substrates were treated in oxygen plasma prior to film deposition. Afterwards, the substrates were placed onto a spin-coater and rotated at a constant rate of 3000 rpm. Firstly, 100 µL of a 7.4 mM solution of 6DT in toluene were applied to the rotating substrate two times. After this pre-treatment, a GNP layer was deposited by applying 10 µL of a GNP stock solution in n-heptane to the substrate. The concentration of the GNP solutions corresponded to an absorbance of 0.2 to 0.4 at a wavelength of 450 nm (dilution factor: 1/600, optical path length 10 mm). Afterwards, 10 µL of a 7.4 mM solution of 6DT in methanol were applied two times in order to cross-link the GNPs. The GNP deposition and cross-linking steps represent one deposition cycle. The GNP films used to form the freestanding nanoparticle composites (membranes) of the sensors used in the present examples were fabricated by applying several consecutive deposition cycles to provide films with thicknesses between 20-80 nm. Between all applications of the solutions, a delay of about ~30 s was kept. Finally, the GNP films were immersed into a methanolic solution of 6DT (7.4 mM) overnight and subsequently rinsed with acetone and dried in a nitrogen flow.

The thickness of the cross-linked GNP membranes was measured according to the procedure described by Schlicke et al. in *Nanotechnology* 2011, 22, 305303. Briefly, a section of the substrate-supported GNP film was scratched using a cannula and two atomic force microscopy (AFM) images were acquired at different positions at the edges of the scratches. From each image several step profiles were extracted and the step heights were averaged to yield the GNP film thickness.

In the frame of the present examples, two cross-linked GNP films (in the following films (A) and (B)) were fabricated according to the procedure described above. It was found that the films (A) and (B) had thicknesses of (44±1) nm and (39±1) nm, respectively (as measured according to the procedure described above).

5.3 Fabrication of Electrode Microstructures

The three-dimensional electrode microstructures acting as support for the freestanding GNP composite materials (membranes) were fabricated in a three-layer photolithography process, similar to that described by Schlicke et al. in *Nanoscale* 2016, 8(35), 15880-15887, which is herein incorporated by reference.

Firstly, a Ti/Au back-electrode layer was deposited onto an oxidized silicon wafer. Afterwards, an insulating layer (SU-8 photoresist) containing cylindrical or square-shaped microcavities (one or more) acting as support for the freestanding membranes was fabricated. In a third step, gold electrodes were deposited on top of the SU-8 layer for electronically contacting the freestanding membranes.

Fabrication of the Back Electrodes:

Firstly, layers of titanium and gold (about 10 nm and about 40 nm, respectively) were deposited onto a thermally oxidized silicon wafer by thermal evaporation (oerlikon leybold UNIVEX 350G). Afterwards, a layer of AZ ECI 3012 positive photoresist was deposited via spin-coating (3000 rpm). The coated wafer was then soft-baked at 90° C. for 90 s and exposed using a Karl Süss MJB-3 mask aligner and a photomask providing the back electrode structure. The resist layer was post-exposure baked at 110° C. for 90 s and developed using AZ 726 MIF developer for 1 min. The sample was rinsed in demineralized water and dried in a nitrogen flow. Exposed sections of the gold layer were then etched using a KI:I$_2$:H$_2$O mixture (4:1:200, m:m:m). The titanium adhesive layer was afterwards removed by immersion of the wafer into concentrated hydrochloric acid (37%) at 42° C. for 60 min. Residual photoresist was removed using N-methyl-2-pyrrolidone or acetone and water.

Fabrication of the SU-8 Microcavities:

The wafer supporting the fabricated back electrode structures was coated with SU-8 2015 negative photoresist by spin-coating (3000 rpm) and soft-baked. Exposure of the resist layer was performed using a Karl Süss MJB-3 mask aligner after aligning a photomask providing the cavity structures (e.g. cylindrical structures or else) with the respective back electrode structures and applying an optical 360 nm long-pass filter. The wafer was post-exposure baked. Development of the SU-8 layer was performed using mr-dev600 developer solution and stopped by rinsing the structure in isopropyl alcohol and water. Afterwards the samples were treated with oxygen plasma to clean the SU-8 surface. Finally, the resist layer was hard-baked by ramping the sample temperature from 120° C. to 200° C. and holding it for 20 min.

The procedure described above was used to form SU-8 structures having either a 4×4 array of cylindrical microcavities with a depth of ~10 μm, or one square-shaped microcavity having an edge length of ~100 μm and a depth of ~10 μm. In this exemplary structure, the depth of the microcavities is controlled by the SU-8 layer thickness.

Fabrication of the Top Electrodes:

Gold top electrodes were fabricated following a lift-off process. Firstly, a layer of AZ 2035 negative photoresist was deposited onto the wafer containing the back electrodes and SU-8 microcavity structures by spin-coating (2000 rpm) and then soft-baked. The deposition step was repeated to fully cover the three-dimensional structures with photoresist. Following the second deposition, the samples were again soft baked. Exposure of the resist layer was then performed using a Karl Süss MJB-3 mask aligner after aligning a photomask providing the top electrode structures with the respective back electrode structures. Following a post-exposure bake for 60 s at 120° C., the resist layer was developed using AZ 726 MIF developer for 120 s and rinsed using demineralized water. Optionally, the exposed SU-8 regions were cleaned in an oxygen plasma. A gold layer (~40 nm thickness) was deposited onto the wafer by thermal evaporation (oerlikon leybold UNIVEX 350G) and structured by a lift-off process, removing the gold layer from the sample sections covered with AZ 2035 photoresist by dissolving the latter in TechniStrip NI555 at 60° C. for 60 min. The finalized microstructures were rinsed with demineralized water and dried in a nitrogen flow.

5.4 Fabrication of Sensors & Experimental Setup

Fabrication of Chemical Sensors:

Two distinct chemical sensors (CS1 and CS2) were fabricated in order to evaluate the method of the present invention. The respective chemical sensors comprised:
- CS1: a freestanding 6DT cross-linked GNP membrane (film (A), thickness=(44±1) nm) suspended over a cylindrical microcavity as part of a 4×4 microcavity array (circular aperture; diameter ~120 μm, depth ~10 μm);
- CS2: a freestanding GNP membrane (film (B), thickness=(39±1) nm) suspended over one square-shaped microcavity (square aperture; edge length ~100 μm, depth ~10 μm).

The chemical sensors were fabricated using the electrode microstructures described above. Following the deposition of the crosslinked GNP films onto glass substrates by spin-coating (see section 5.2), the glass slides coated with the 6DT cross-linked GNP films A and B were cut into several pieces. A piece of each GNP film was lifted off its initial glass substrate by flotation on demineralized water. After keeping the substrate with the film floating on the water surface for a few days, the film could be detached from its substrate by immersion into the aqueous phase rendering the film free-floating at the liquid-air interface. Subsequently, the film was skimmed using the electrode microstructure and allowed to dry. Alternatively, the film floating at the air-liquid interface could also be transferred onto the 3D-structured electrodes using the Langmuir-Schaefer technique. Finally, the substrates supporting the microelectrodes covered with the cross-linked GNP films were fixed on a custom-designed printed circuit board (PCB) and connected by wire bonding (back electrodes) and silver paste (top electrode).

Fabrication of a Chemiresistor:

Gold electrodes having a thickness of about ~100 nm were deposited onto a second glass substrate-supported piece of the spin-coated GNP film (A) by thermal evaporation according to the procedure described by Schlicke et al. in *Nanotechnology* 2011, 22, 305303. A shadow mask was applied during evaporation, yielding a conductive channel of cross-linked GNPs having a length of 400 μm and a width of 11 mm. Current-voltage data of the chemiresistor was acquired using an Agilent 4156C semiconductor parameter analyzer. The device showed a conductivity of ~0.1 S cm$^{-1}$, which was calculated from the measured conductance by taking into account the geometry of the channel.

Fabrication of a QCM Sensor:

A section of the GNP film A was detached from one of the several coated glass slide pieces and deposited onto the active area on one side of a QCM sensor (AT cut quartz, 10 MHz fundamental resonance frequency, ~28 mm$^2$ electrode area) using the same transfer technique as described above for the transfer of the GNP films onto 3D-structured microelectrodes.

Experimental Setup:

The fabricated chemical sensors were mounted on custom-designed printed circuit boards (PCBs). Electric contacts to the top electrode and the back electrode were made using silver paint or wire bonding, respectively. The PCB mounted with an array of 4×4 chemical sensors was equipped with contacts, suitable for addressing a QCM and a chemiresistor (fabricated as described above) on its backside. The PCBs were also equipped with pins, suitable for attachment to a socket in a sensor test cell.

A schematic drawing of the sensor test cell with (I) a chemical sensor, (II) a chemiresistor, and (III) a QCM (as used in Examples 1, 5 and 6, see below) is depicted in FIG. 9.

With reference to FIG. 9, (I) a chemical sensor comprising a freestanding nanoparticle composite material with interferometric deflection readout (according to the invention), (II) a chemiresistive sensor comprising a nanoparticle composite material (prior art) and (III) a quartz crystal microbalance (QCM) coated with a nanoparticle composite material (prior art), each connected to respective suitable readout electronics, were placed in a sensor test cell equipped with pressure and temperature sensors, and with a peripheral system enabling the introduction of nitrogen gas, or nitrogen gas mixed with solvent vapors at defined concentrations, and to control the cell's internal pressure. The test cell includes feedthroughs for connecting the sensors to external measurement hardware.

The chemical sensor(s) were supplied with a drive signal, provided by a function generator (Keysight 33521B) and amplified by a high-voltage amplifier (Falco Systems WMA-300). Movements of the membrane were monitored using a laser interferometer (Nanovibration Analyzer NA, SIOS GmbH). For these measurements the laser was directed through a glass window onto the center of the freestanding GNP membrane of the chemical sensor (in the case of sensor CS1 one of the chemical sensors being part of the array of 4×4 chemical sensors).

The chemiresistor was connected to a Keithley 2601A sourcemeter, applying a constant 1 V bias and continuously monitoring its resistance by measuring the resulting current through the channel of cross-linked GNPs.

The QCM was connected to an Agilent E5100A network analyzer in order to monitor the resonance spectrum of the quartz crystal. The network analyzer was locked onto the falling edge of the phase signal to detect shifts of the resonance frequency.

The sensor test cell was equipped with a digital temperature sensor (DS18b20) and a pressure sensor (oerlikon leybold TTR 101N), which includes a MEMS Pirani gauge and a piezo membrane pressure sensor. The latter is suitable to measure the absolute cell pressure in the given pressure range independently of the gas type present.

In case of measurements under reduced pressure, the outlet of the sensor test cell was connected to a rotary vane pump via a liquid nitrogen cooling trap. Nitrogen zero gas (ZG), or an analyte-enriched nitrogen gas mixture (AG) with adjustable molar fractions of analyte $x_{analyte}$ were supplied by a commercial gas calibration system (MCZ Umwelttechnik CGM2000) at approximately atmospheric pressure. A portion of this gas was fed to the sensor cell's inlet by a needle valve, which was adjusted to yield a constant absolute pressure of $P_{abs}$=20 mbar within the sensor cell. The calibration system was set to provide alternatingly 8 min AG with molar analyte fractions of $x_{analyte}$=1000, 4000, 7000 and 10000 ppm spaced by an 8 min application of ZG. This yields alternating analyte partial pressure transients in the vacuum cell of $P_{analyte}$=$x_{analyte}P_{abs}$. In the case of measurements under ambient pressure, ZG and AG gas were sourced from the gas calibration system to the sensor test cell by connecting a draining pump system (flow rate 400 mL/min) to its outlet.

5.5 Determination of the Quality Factor Q

In case of measurements under reduced pressure, the quality factor of the membrane resonators could be determined by the procedure as described by Schlicke et al. in *Nanoscale* 2016, 8, 15880-15887. For device CS1 a quality factor of 45 was determined under a nitrogen atmosphere at reduced pressure of ~20 mbar.

5.6 Example 1—Determination of the Fundamental Resonance Frequency & Dynamic Detection of Toluene (1000, 4000, 7000, and 10000 ppm)

A PCB mounted with chemical sensor CS1 (and a QCM) was placed into the sensor test cell. The chemical sensor was excited by electrostatic forces using a drive voltage V(t) (equation 1), formed by a sine function with an amplitude $V_{AC}$ and a linearly swept drive frequency $f_d$ and a DC component $V_{DC}$. Here, the DC component was set to a larger value than the AC amplitude, to avoid a zero-crossing of the net voltage and hence of the electrostatic forces acting on the freestanding membrane. The drive frequency was continuously swept in the spectral range of interest ("frequency sweeping").

$$V(t)=V_{DC}V_{AC}\sin(2\pi f_d t) \qquad (1)$$

Synchronized with the duration of the sweep, deflection time traces of the membrane were continuously acquired using the Nanovibration Analyzer NA laser interferometer (SIOS GmbH). Time traces with a total of 65536 data points were repeatedly recorded with a sampling frequency of ~2 MHz. The excitation voltages were set to $V_{DC}$=7.5 V and $V_{AC}$=3.75 V and the drive frequency sweep range was set between 100 and 450 kHz. The time series of amplitude spectra was obtained by computing the fast Fourier transform of the deflection time traces. Resonance frequencies were extracted by fitting Lorentzians to the fundamental resonance peaks in the frequency range of ±40 kHz at the spectra's maximum amplitude points. At the beginning of the experiment, a fundamental resonance frequency of ~215 kHz was found for the sensor under ZG. An absolute pressure of $P_{abs}$=20 mbar was maintained within the sensor test cell during the experiment.

The gas calibration system was set to first provide 8 min ZG, and then, alternatingly, to provide 8 min AG with molar toluene fractions (partial pressures) of $x_{toluene}$=1000 (2 Pa), 4000 (8 Pa), 7000 (14 Pa) and 10000 ppm (20 Pa) spaced by 8 min applications of ZG over the whole duration of the experiment.

The frequency shift observed in this experiment at the maximum toluene molar fraction (partial pressure) of 10000 ppm (20 Pa) is depicted in FIG. 5, showing the amplitude spectra of the fundamental resonance mode of the sensor under ZG, and under AG. As can be seen, a pronounced downshift of the resonance frequency was observed. The observed downshift of the resonance frequency can be attributed to the reduction of the GNP membrane's tension (pre-stress) and/or elastic modulus due to toluene sorption, as shown further below.

For a circular membrane oscillating in vacuum, the fundamental resonance frequency can be determined by equation (1) (cf. Adiga et al. *Appl. Phys. Lett.* 2011, 99, 253103):

$$f_{0,1} = \frac{2.405}{2\pi a} \sqrt{\frac{\sigma}{\rho}} \quad (2)$$

In equation (2), $\alpha$ denotes the membrane radius, a is the membrane pre-stress and $\rho$ its density. By monitoring the mass uptake of another GNP film fragment throughout the experiment using a quartz crystal microbalance (QCM), the impact of the membrane's mass change on its fundamental resonance frequency could be approximated. Shifts of the QCM resonance frequency were lower than 2 Hz, as visible in FIG. 10 and FIG. 11. Taking into account the specifications of the QCM a 2 Hz shift corresponds to a mass uptake of ~2.5 ng for the film which was deposited onto the QCM sensor. This corresponds to a mass uptake of the membrane section with the size of the ~120 µm circular resonator of ~1 pg. Taking into account only this mass change of the membrane (and the original density of the membrane estimated as ~9.3 g cm$^{-3}$), frequency shifts of only a few tens of Hz are expected using equation (2).

The results depicted in FIG. 6 show the shift of the fundamental resonance frequency of the GNP membrane $f_0$ as a function of time when dosing the membrane with AG of different concentrations, as indicated. A much stronger downshift in resonance frequency of up to ~10 kHz, i.e. about three orders of magnitude larger than expected by the gravimetric effect, is observed. Thus, this finding clearly demonstrates that a change in the membrane's pre-stress and/or elastic modulus upon sorption of analyte plays a crucial role in the sensing mechanism.

In particular, a downshift of $\Delta f_0$~1.5 kHz was observed when AG with a molar toluene fraction of $x_{toluene}$=1000 ppm was supplied. At the total pressure of 20 mbar this molar fraction corresponds to a partial analyte pressure of only $20\times10^{-3}$ mbar and, thus, this result demonstrates that the method of the present invention allows the detection of toluene with excellent sensitivity. Furthermore, the resonance frequency rapidly increased and returned to its initial resonance frequency when ZG was supplied instead of AG. These results demonstrate the excellent resolution achieved by the method of the present invention, and also illustrate its applicability for real-time "on the spot" gas monitoring.

5.7 Example 2—Quasi-static Detection of Toluene (10000 ppm)

A PCB mounted with chemical sensor CS2 was placed in the sensor test cell. The calibration system was set to alternatingly provide 8 min AG with molar analyte fractions of $x_{toluene}$=10000 ppm spaced by an 8 min application of ZG (all under atmospheric pressure, i.e. ~1 bar).

Continuously, groups of 1 second pulses of increasing DC voltages (20, 40, 60, 80 and 100 V) were applied to deflect the cross-linked GNP membrane of the chemical sensor by electrostatic forces. A laser interferometer was directed onto the center of the membrane to record the deflection h of the freestanding membrane.

The recorded deflection of the GNP membrane under ZG and AG ($x_{toluene}$=10000 ppm) using pulses of increasing DC voltage (dashed and solid line, respectively) is shown in FIG. 7. As can be seen, the deflection of the GNP membrane significantly increased when the chemical sensor was exposed to AG. The deflection increase can be attributed to a change in the tension (pre-stress and/or elastic modulus) of the GNP membrane due to analyte sorption.

5.8 Example 3—Quasi-Static Vs. Dynamic Detection of Toluene (1000, 4000, 7000 and 10000 ppm)

The quasi-static response of chemical sensor CS2 to increasing concentrations of toluene was measured in the same manner as in Example 2 (by continuously measuring deflection transients of the membrane induced by groups of five 1 s voltage pulses: 20, 40, 60, 80 and 100 V), except that the gas calibration system was set to provide alternatingly 8 min ZG and AG transients with toluene concentrations (partial pressures) of $x_{toluene}$=1000 (2 Pa), 4000 (8 Pa), 7000 (14 Pa) and 10000 ppm (20 Pa) at a constant absolute pressure of $P_{abs}$=20 mbar.

The central-point deflection h of a square membrane due to an applied pressure difference P can be computed by the following equation (3) (cf. Vlassak et al. *J. Mater. Res.* 1992, 7, 3242):

$$P = c_1 \frac{\sigma_0 t}{b^2} h + c_2 \frac{Et}{b^4(1-v)} h^3 \quad (3)$$

Here, $\sigma_0$ is the membrane's pre-stress, t denotes its thickness and b the cavity's half edge length. v is the Poisson ratio and E the membrane's elastic modulus (Young's modulus). For square membranes $c_1$=3.393, and $c_2$ is another constant.

For small deflections, the pressure can be replaced by the electrostatic force per area, induced by the approximately homogeneous electric field between the membrane and the counter electrode (cf. Schlicke et al. *ACS Appl. Mater. Interfaces* 2015, 7, 15123). Also, for small deflections, the second term of equation (3) can be neglected. This yields an approximated proportionality between $V^2$ and h:

$$\frac{\epsilon V^2}{2d^2} = \frac{3.393 \sigma_0 t}{b^2} h \quad (4)$$

Here, V is the applied bias voltage and d is the distance between the membrane and the back electrode (counter electrode), defined approximately by the depth of the cavity covered by the membrane. $\epsilon$ represents the permittivity of the cavity volume. Using equation (4), the deflection transient groups, repeatedly recorded over the course of the experiment were evaluated. From slope fits to the $V^2(h)$ datasets, a time series of $\sigma_0$ (corresponding to the pre-stress of the freestanding GNP membrane) was obtained.

The dynamic response of chemical sensor CS2 to increasing concentrations of toluene was also measured using the frequency sweeping procedure described above ($V_{DC}$=10 V, $V_{AC}$=5 V, frequency range: 100 kHz-1 MHz, data points: 65536) (i.e. by exciting the membrane by an AC voltage) and observing the membrane's oscillations by laser interferometry. Neglecting sorption-induced changes in the membrane's mass density, the pre-stress a was computed using equation (5), describing the fundamental resonance frequency f of a clamped square membrane in vacuum (cf. Zhang et al. *Appl. Phys. Lett.* 2015, 106, 063107):

$$f = \frac{1}{2}\sqrt{\frac{\sigma}{\rho}}\sqrt{\frac{1^2}{(2b)^2} + \frac{1^2}{(2b)^2}} \quad (5)$$

The results of these experiments are depicted in FIG. 8, showing the pre-stress time traces of the chemical sensor CS2 actuated by a quasi-static actuating force (by applying 1 s DC voltage pulses; dashed line) and a dynamic actuating force (by applying an AC voltage; solid line).

5.9 Example 4—Dynamic Detection of Toluene Using Chemical Sensor, Chemiresistor and QCM As in example 1, a PCB mounted with chemical sensor CS1, a chemiresistor, and a QCM fabricated as described above, was placed into the sensor test cell. The experimental setup used in this experiment is depicted in FIG. 9. The experiment was conducted as described in example 1. As in example 1, a constant absolute pressure $P_{abs}$=20 mbar was maintained within the sensor test cell.

The results of this experiment are depicted in FIG. 10, showing the fundamental resonance frequency $f_0$ and the resonance frequency shift $\Delta f_0$ of sensor CS1 as a function of time (respective traces (a) and (b)).

Simultaneously, the responses of the chemiresistor, i.e. the electrical resistance, and QCM, i.e. shifts of the fundamental resonance frequency, were also monitored. The results are depicted in FIG. 10, showing the measured electrical resistance R of the chemiresistor (trace (c)) as well as the corresponding relative resistance change $\Delta R/R_0$ (trace (d)), and the measured resonance frequency shift $\Delta f_{QCM}$ of the QCM (trace (e)). Traces (f) and (g) display the total pressure $P_{abs}$ and the temperature T, respectively, measured within the sensor cell.

These results demonstrate that the method of the present invention allows the detection of toluene with excellent sensitivity. In particular, a pronounced resonance frequency downshift of $\Delta f_0$=~1.5 kHz was observed when AG with a toluene molar fraction of $x_{toluene}$=1000 ppm was supplied. In contrast, the chemiresistor delivered only a weak signal (cf. traces (c) and (d)), whereas the QCM failed to clearly detect the presence of toluene (cf. trace (e)). Consequently, these results demonstrate a significant improvement of sensitivity achieved by the method of the present invention.

The responses of chemical sensor CS1 to increasing concentrations of toluene were used to produce the calibration curve shown in FIG. 12, as well as the transient response kinetics shown in FIG. 13.

5.10 Example 5—Dynamic Detection of Water using Chemical Sensor, Chemiresistor and QCM The same experiment as in Example 4 was reproduced, except that water was used as the analyte instead of toluene.

That is, the gas calibration system was set to first provide 8 min ZG, followed by an 8 min application of AG with molar water fractions (partial pressures) of $x_{water}$=1000 (2 Pa), 4000 (8 Pa), 7000 (14 Pa), and 10000 ppm (20 Pa) spaced by an 8 min application of ZG, and followed again by application of ZG. A constant absolute pressure $P_{abs}$=20 mbar was maintained within the sensor test cell.

The responses of the chemical sensor CS1, the chemiresistor, and the QCM were monitored in the same manner as described in Example 4. The results are depicted in FIG. 11, showing the fundamental resonance frequency $f_0$ of chemical sensor CS1 (trace (a)), the corresponding fundamental resonance frequency shift $\Delta f_0$ (trace (b)), the electrical resistance R of the chemiresistor (trace (c)), the corresponding relative resistance shift $\Delta R/R_0$ (trace (d)), and the fundamental resonance frequency shift $\Delta f_{QCM}$ of the QCM (trace (e)). Traces (f) and (g) display the total pressure $P_{abs}$ and the temperature T, respectively, measured within the sensor cell.

As can be seen in FIG. 11, the method of the present invention allows the detection of water with excellent sensitivity (cf. traces (a)-(b)). In contrast, the chemiresistor and the QCM failed to detect water, even when it was present at relatively high concentrations (cf. traces (c)-(e)). Therefore, these results demonstrate a significant improvement in terms of sensitivity achieved by the method of the present invention.

The responses of chemical sensor CS1 to increasing concentrations of water were used to produce the calibration curve shown in FIG. 12, as well as the transient response kinetics shown in FIG. 13.

5.11 Example 6—Dynamic Detection of Toluene, 4-methylpentan-2-one, 1-propanol, and Water using Chemical Sensor and Chemiresistor The same experiment as in Examples 4 and 5 was reproduced, except that 4-methylpentan-2-one (4M2P) and 1-propanol were used as analytes. That is, the gas calibration system was set to first provide 8 min ZG, followed by an 8 min application of AG with molar fractions (partial pressures) of 1000 (2 Pa), 4000 (8 Pa), 7000 (14 Pa), and 10000 ppm (20 Pa) of 4M2P or 1-propanol spaced by an 8 min application of ZG, and followed again by application of ZG. A constant absolute pressure $P_{abs}$=20 mbar was maintained within the sensor test cell.

The respective responses of chemical sensor CS1 to increasing concentrations of 4M2P and 1-propanol (and two other analytes) were used to produce the calibration curves shown in FIG. 12, as well as the transient response kinetics shown in FIG. 13.

Furthermore, the chemical sensor CS1 and the chemiresistor (which were prepared from the same cross-linked nanoparticle composite material) have different chemical selectivities. This is shown in FIG. 14 by the different relative signal intensities measured after exposing the sensors for 8 minutes to different analyte vapors, as indicated. Therefore, the relative signal intensities of the two sensors exposed to the same test sample correspond to a signal pattern which can be used for recognizing a target analyte. In addition, as mentioned above, the distinct response kinetics of the sensor CS1 observed when exposing this sensor to different analytes (FIG. 13) can be utilized for analyte recognition.

The invention claimed is:
1. Method for detecting an analyte with a chemical sensor, comprising the steps of:

(i) exposing the chemical sensor comprising a permeable freestanding nanoparticle composite material to the analyte; and
(ii) measuring a sensor signal caused by a change of the elastic modulus and/or pre-stress of the freestanding nanoparticle composite material by a detection device or equipment;
   wherein the chemical sensor comprises a substrate, and the substrate comprises one or more microcavities, onto which the freestanding nanoparticle composite material is suspended as a membrane; and
   wherein the sensor signal that is caused by a change of elastic modulus and/or pre-stress of the freestanding nanoparticle composite material is detected by applying a force and measuring a response selected from the group consisting of:
      applying a quasi-static actuating force on the composite material selected from the group consisting of an electrostatic force and a magnetic force; and measuring a response of the composite material to the actuating force; and
      applying an electrostatic force induced by an alternating (AC) electric field having a frequency between 1 kHz to 10 GHz, such that the composite material oscillates at one of its resonance frequencies; and
      measuring a shift of the resonance frequency or any change in amplitude or phase.

2. The method of claim 1, wherein the freestanding nanoparticle composite material comprises nanoparticles formed from components selected from the group consisting of:
   (a) a metal;
   (b) a metal oxide;
   (c) a semiconductor;
   (d) a carbon material selected from the group consisting of carbon black, carbon nanotubes, graphite, and a mono- or multilayered two-dimensional carbon material selected from the group consisting of flakes of graphene, graphene oxide, and reduced graphene oxide;
   (e) a metal chalcogenide, selected from the group consisting of a transition metal chalcogenide and, a mono- or multilayered two-dimensional metal chalcogenide material; and
   any combination thereof.

3. The method of claim 2, wherein the shape of the nanoparticles is selected from the group consisting of spherical, polyhedral, star-shaped, elongated shape rod-, tube- fiber-shaped, and plate or sheet-like and wherein the nanoparticles have at least one dimension with a length lower than 100 nm.

4. The method of claim 1, wherein the freestanding nanoparticle composite material comprises a matrix in which the nanoparticles are dispersed or interconnected with each other; and
   wherein the matrix comprises a material selected from the group consisting of:
   A) organic polymers;
   B) polysiloxanes;
   C) organic ligands selected from the group consisting of mono-, bi- and polyfunctional organic ligands that are able to attach to the surface of the nanoparticles with at least one functional group;
   D) bi- or polyfunctional organic cross-linkers that are able to attach to the surface of the nanoparticles with at least two functional groups.

5. The method of claim 4, wherein the matrix is attached to the surface of the nanoparticles by a bond selected from the group consisting of covalent bonds, ionic bonds, coordinative covalent (dipolar) bonds and multiple dipolar interactions; and
   wherein the matrix is attached to the surface of the nanoparticles via carbon-to-nanoparticle bonds or via one or more functional groups, selected from the group consisting of thiol, disulfide, carbamate, thiocarbamate, dithiocarbamate, amino, carboxylic acid, hydroxyl, polyether, isocyanide, dihydroxyphenyl, phosphine, phosphine oxide, and phosphonic acid groups.

6. The method of claim 4, wherein the nanoparticles are cross-linked with a bi- or polyfunctional organic cross-linker having functional groups that attach to the surface of the nanoparticles selected from the group consisting of thiol, disulfide, amino, carboxylic acid, thiocarbamate, dithiocarbamate, hydroxyl, isocyanide, dihydroxyphenyl, phosphine, phosphine oxide, and phosphonic acid groups.

7. The method of claim 1, wherein the sensor signal that is caused by a change of elastic modulus, pre-stress of the freestanding nanoparticle composite material, or both is detected by measuring a change in a feature selected from the group consisting of structure, topography, shape, and size of the composite material.

8. The method of claim 1, wherein the response of the freestanding nanoparticle composite material to the actuating force applied thereon is measured by a method selected from the group consisting of:
   ($\alpha$) detecting light reflected or emitted from or scattered by the composite material;
   ($\beta$) measuring a change of the electrical resistance/impedance of the composite material;
   ($\gamma$) measuring a change of the capacitance of the composite material arranged with one or more proximate electrodes; and
   ($\delta$) measuring the magnetic field in proximity of the composite material.

9. The method of claim 1, further comprising the steps of:
   (iii) calibrating a chemical sensor comprising the permeable freestanding nanoparticle composite material by measuring the sensor signal when exposing the chemical sensor to a reference sample of the analyte at various known concentrations; and
   (iv) comparing the sensor signal measured by exposing the chemical sensor to the test sample of the analyte to the calibration data measured in step (iii) to determine the concentration of the analyte in the test sample.

10. The method of claim 1, wherein the method further comprises the steps of:
   (v) adjusting the chemical selectivity of the freestanding nanoparticle composite material to the analyte before (i) exposing the chemical sensor to the analyte;
   (vi) calibrating the chemical sensor comprising the permeable freestanding nanoparticle composite material by measuring the sensor signal when exposing the chemical sensor to the reference sample of the analyte; and
   (vii) comparing the sensor signal to the calibration data measured in step (vi) to recognize the analyte in the test sample.

11. The method of claim 1, wherein the analyte is in a gas phase.

12. The method of claim 1, wherein the method comprises exposing an array of chemical sensors comprising at least two chemical sensors, to the analyte thus affording a signal pattern that allows recognition of the analyte;

wherein the individual chemical sensors comprise a permeable freestanding nanoparticle composite material and differ from each other in a way selected from the group consisting of the type of nanoparticles, the chemical composition of the matrix in their respective freestanding nanoparticle composite material, the thickness, geometry, or geometric arrangement of the freestanding nanoparticle composite material, and in their respective detection mode.

13. The method of claim 1, wherein the chemical sensor comprising the permeable freestanding nanoparticle composite material is combined with at least one other chemical or physical sensor having a different signal transduction mechanism.

14. The method of claim 1, wherein the membrane has a thickness lower than 1000 nm.

15. The method of claim 3, wherein the nanoparticles are spherical or polyhedral particles having a respective average diameter or length in at least one dimension lower than 100 nm.

16. The method of claim 7, wherein the change is detected by detecting light reflected, emitted from, or scattered by the composite material.

* * * * *